United States Patent
Castellano

(10) Patent No.: US 6,613,010 B2
(45) Date of Patent: Sep. 2, 2003

(54) MODULAR GAS-PRESSURED NEEDLE-LESS INJECTOR

(75) Inventor: Thomas P. Castellano, Santa Monica, CA (US)

(73) Assignee: PenJet Corporation, Santa Monica, CA (US)

(*) Notice: Subject to any disclaimer, the term of this patent is extended or adjusted under 35 U.S.C. 154(b) by 8 days.

(21) Appl. No.: 09/834,476

(22) Filed: Apr. 13, 2001

(65) Prior Publication Data

US 2002/0151840 A1 Oct. 17, 2002

(51) Int. Cl.[7] ................................................. A61M 5/30
(52) U.S. Cl. .............................. 604/68; 604/70; 604/73; 604/140; 604/147; 604/191; 604/223; 128/200.16
(58) Field of Search .............................. 604/68, 69, 70, 604/72, 136, 140, 141, 143, 144, 145, 181, 187; 222/162, 389, 399; 128/200.14, 200.21, 200.23

(56) References Cited

U.S. PATENT DOCUMENTS

| | | |
|---|---|---|
| 1,997,129 A | 4/1935 | Taylor et al. |
| 2,221,739 A | 11/1940 | Reiter |
| 2,605,763 A | 8/1952 | Smoot |
| 2,632,445 A | 3/1953 | Kas, Sr. |
| 2,642,062 A | 6/1953 | May |
| 2,680,439 A | 6/1954 | Sutermeister |
| 2,695,023 A | 11/1954 | Brown |
| 2,718,299 A | 9/1955 | Atwater et al. |
| 2,754,818 A | 7/1956 | Scherer |
| 3,110,310 A | 11/1963 | Cislak |
| 3,131,692 A | 5/1964 | Love |
| 3,141,583 A | 7/1964 | Mapel et al. |
| 3,293,749 A | 12/1966 | George et al. |
| 3,348,545 A | 10/1967 | Sarnoff et al. |
| 3,481,510 A | 12/1969 | Allen |
| 3,507,276 A | 4/1970 | Burgess |
| 3,517,668 A | 6/1970 | Brickson |
| 3,557,784 A | 1/1971 | Shields |
| 3,583,399 A | 6/1971 | Ritsky |
| 3,688,765 A | 9/1972 | Gasaway |
| 3,695,266 A | * 10/1972 | Lussier ........................ 222/471 |

(List continued on next page.)

FOREIGN PATENT DOCUMENTS

| | | |
|---|---|---|
| CA | 1103314 | 2/1978 |
| CA | 1 258 019 | 8/1989 |
| CH | 293302 | 9/1953 |
| DE | 730971 | 1/1943 |
| DE | 1 070 784 | 12/1959 |
| DE | 22140 | 10/1961 |
| EP | 0 037 696 A1 | 3/1981 |
| EP | 0 143 895 A1 | 8/1984 |
| EP | 0 220 146 A1 | 10/1986 |
| EP | 0 295 917 A1 | 6/1988 |
| EP | 0 327 910 A2 | 1/1989 |
| EP | 0 347 190 A1 | 6/1989 |
| EP | 0 368 191 A1 | 11/1989 |
| EP | 0 416 975 A1 | 8/1990 |

(List continued on next page.)

Primary Examiner—Gene Mancene
Assistant Examiner—John Fristoe
(74) Attorney, Agent, or Firm—Pillsbury Winthrop LLP

(57) ABSTRACT

A needle-less injector suitable for injecting fluid through a surface includes a housing, a driver, an engine and a trigger. The housing contains a fluid and the engine contains a compressed gas. Upon application of sufficient force to the trigger, the compressed gas is released from the engine forcing the driver through the interior of the housing, expelling the liquid from the housing at a speed sufficient to pierce an injection surface. In one embodiment, the needle-less injector includes a mechanism for mitigating the kick-back associated with releasing compressed gas from the engine. In another embodiment, the housing includes finger rests that provide stability and resistance to activate the device. In another embodiment, the engine is fitted with a reusable valve. In another embodiment, a safety clamp is included on the housing, preventing accidental activation of the device,

48 Claims, 16 Drawing Sheets

U.S. PATENT DOCUMENTS

| | | | | |
|---|---|---|---|---|
| 3,853,125 | A | * 12/1974 | Clark et al. | ............ 604/70 |
| 3,859,996 | A | 1/1975 | Mizzy et al. | |
| 3,894,663 | A | 7/1975 | Carhart et al. | |
| 3,977,574 | A | 8/1976 | Thomas | |
| 4,022,207 | A | 5/1977 | Citrin | |
| 4,031,892 | A | 6/1977 | Hurschman | |
| 4,033,378 | A | 7/1977 | Pauliukonis | |
| 4,099,548 | A | 7/1978 | Sturm et al. | |
| 4,114,619 | A | 9/1978 | Wagner | |
| 4,139,008 | A | 2/1979 | Wagner | |
| 4,146,029 | A | 3/1979 | Ellinwood, Jr. | |
| 4,169,474 | A | 10/1979 | Wagner | |
| 4,284,077 | A | 8/1981 | Wagner | |
| 4,333,458 | A | 6/1982 | Margulies et al. | |
| 4,338,980 | A | 7/1982 | Schwebel et al. | |
| 4,393,870 | A | 7/1983 | Wagner | |
| 4,395,921 | A | 8/1983 | Oppenlander | |
| 4,413,760 | A | 11/1983 | Paton | |
| 4,415,101 | A | 11/1983 | Shapiro et al. | |
| 4,425,121 | A | 1/1984 | Young et al. | |
| 4,431,117 | A | * 2/1984 | Genbauffe et al. | ...... 137/505.39 |
| 4,435,173 | A | 3/1984 | Siposs et al. | |
| 4,444,560 | A | 4/1984 | Jacklich | |
| 4,457,712 | A | 7/1984 | Dragan | |
| 4,470,317 | A | 9/1984 | Sabloewski et al. | |
| 4,475,905 | A | 10/1984 | Himmelstrup | |
| 4,498,904 | A | 2/1985 | Turner et al. | |
| 4,526,294 | A | 7/1985 | Hirschmann et al. | |
| 4,529,401 | A | 7/1985 | Leslie et al. | |
| 4,538,616 | A | 9/1985 | Rogoff | |
| 4,573,970 | A | 3/1986 | Wagner | |
| 4,581,022 | A | 4/1986 | Leonard et al. | |
| 4,592,745 | A | 6/1986 | Rex et al. | |
| 4,596,556 | A | 6/1986 | Morrow et al. | |
| 4,600,403 | A | 7/1986 | Wagner | |
| 4,613,328 | A | 9/1986 | Boyd | |
| 4,659,327 | A | 4/1987 | Bennett et al. | |
| 4,664,128 | A | 5/1987 | Lee | |
| 4,676,781 | A | 6/1987 | Phillips et al. | |
| 4,680,027 | A | 7/1987 | Parsons et al. | |
| 4,710,172 | A | 12/1987 | Jacklich et al. | |
| 4,710,178 | A | 12/1987 | Leonard et al. | |
| 4,722,728 | A | 2/1988 | Dixon | |
| 4,743,299 | A | 5/1988 | Chu | |
| 4,790,824 | A | 12/1988 | Morrow et al. | |
| 4,820,287 | A | 4/1989 | Leonard | |
| 4,834,149 | A | 5/1989 | Fournier et al. | |
| 4,865,591 | A | 9/1989 | Sams | |
| 4,874,367 | A | 10/1989 | Edwards | |
| 4,883,472 | A | 11/1989 | Michel | |
| 4,913,699 | A | 4/1990 | Parsons | |
| 4,936,833 | A | 6/1990 | Sams | |
| 4,941,880 | A | 7/1990 | Burns | |
| 4,950,246 | A | 8/1990 | Muller | |
| 4,959,056 | A | 9/1990 | Dombrowski et al. | |
| 4,998,570 | A | 3/1991 | Strong | |
| 5,009,634 | A | 4/1991 | Feldman et al. | |
| 5,009,637 | A | 4/1991 | Newman et al. | |
| 5,024,656 | A | 6/1991 | Gasaway et al. | |
| 5,047,044 | A | 9/1991 | Smith et al. | |
| 5,050,612 | A | 9/1991 | Matsumura | |
| 5,064,413 | A | 11/1991 | McKinnon et al. | |
| 5,069,668 | A | 12/1991 | Boydman | |
| 5,085,642 | A | 2/1992 | Sarnoff et al. | |
| 5,092,842 | A | 3/1992 | Bechtold et al. | |
| 5,102,393 | A | 4/1992 | Sarnoff et al. | |
| 5,104,380 | A | 4/1992 | Holman et al. | |
| 5,112,317 | A | 5/1992 | Michel | |
| 5,114,406 | A | 5/1992 | Gabriel et al. | |
| 5,139,484 | A | 8/1992 | Hazon et al. | |
| 5,180,371 | A | 1/1993 | Spinello | |
| 5,226,895 | A | 7/1993 | Harris | |
| 5,226,896 | A | 7/1993 | Harris | |
| 5,244,461 | A | 9/1993 | Derlien | |
| 5,244,465 | A | 9/1993 | Michel | |
| 5,249,584 | A | 10/1993 | Karkar et al. | |
| 5,254,100 | A | 10/1993 | Huband | |
| 5,256,157 | A | 10/1993 | Samiotes et al. | |
| 5,267,977 | A | 12/1993 | Feeney, Jr. | |
| 5,279,294 | A | 1/1994 | Anderson et al. | |
| 5,279,584 | A | 1/1994 | Dillard, III et al. | |
| 5,279,585 | A | 1/1994 | Balkwill | |
| 5,279,586 | A | 1/1994 | Balkwill | |
| 5,330,430 | A | 7/1994 | Sullivan | |
| 5,342,309 | A | 8/1994 | Hausser | |
| 5,354,287 | A | 10/1994 | Wacks | |
| 5,383,865 | A | 1/1995 | Michel | |
| 5,425,716 | A | 6/1995 | Kawasaki et al. | |
| 5,429,602 | A | 7/1995 | Hauser | |
| 5,445,620 | A | 8/1995 | Haber et al. | |
| 5,480,381 | A | 1/1996 | Weston | |
| 5,503,627 | A | 4/1996 | McKinnon et al. | |
| 5,509,905 | A | 4/1996 | Michel | |
| 5,520,639 | A | 5/1996 | Peterson et al. | |
| 5,536,249 | A | 7/1996 | Castellano et al. | |
| 5,540,664 | A | 7/1996 | Wyrick | |
| 5,569,189 | A | 10/1996 | Parsons | |
| 5,593,388 | A | 1/1997 | Phillips | |
| 5,593,390 | A | 1/1997 | Castellano et al. | |
| 5,630,796 | A | 5/1997 | Bellhouse et al. | |
| 5,649,912 | A | 7/1997 | Peterson | |
| 5,704,911 | A | 1/1998 | Parsons | |
| 5,713,873 | A | 2/1998 | Jehle | |
| 5,728,074 | A | 3/1998 | Castellano et al. | |
| 5,730,723 | A | 3/1998 | Castellano et al. | |
| 5,820,602 | A | 10/1998 | Kovelman et al. | |
| 5,851,198 | A | * 12/1998 | Castellano et al. | ............ 604/68 |
| 5,891,085 | A | * 4/1999 | Lilley et al. | ............ 604/140 |
| 5,891,086 | A | 4/1999 | Weston | |
| 5,891,192 | A | 4/1999 | Castellano | |
| 5,893,397 | A | 4/1999 | Peterson et al. | |
| 5,899,880 | A | 5/1999 | Bellhouse et al. | |
| 5,925,021 | A | 7/1999 | Castellano et al. | |
| 5,957,166 | A | 9/1999 | Safabash | |
| 5,957,886 | A | 9/1999 | Weston | |
| 5,993,412 | A | 11/1999 | Deily et al. | |
| 6,063,053 | A | 5/2000 | Castellano et al. | |
| 6,080,130 | A | * 6/2000 | Castellano | ............ 604/68 |
| 6,096,002 | A | 8/2000 | Landau | |
| 6,132,395 | A | 10/2000 | Landau et al. | |
| 6,135,979 | A | 10/2000 | Weston | |
| 6,145,762 | A | 11/2000 | Orloff et al. | |
| 6,149,625 | A | 11/2000 | Weston et al. | |
| 6,156,008 | A | 12/2000 | Castellano | |
| 6,168,587 | B1 | * 1/2001 | Bellhouse et al. | ............ 604/522 |
| 6,174,304 | B1 | 1/2001 | Weston | |
| 6,309,371 | B1 | * 10/2001 | Deboer et al. | ............ 604/68 |
| 6,406,455 | B1 | * 6/2002 | Willis et al. | ............ 604/191 |

FOREIGN PATENT DOCUMENTS

| | | |
|---|---|---|
| EP | 0 427 457 A2 | 11/1990 |
| FR | 1 149 735 | 12/1957 |
| FR | 1 170 312 | 1/1959 |
| FR | 1378829 | 11/1964 |
| FR | 1 445 659 | 10/1966 |
| FR | 78 05814 | 3/1978 |
| FR | 2 557 445 | 12/1984 |
| FR | 2 749 169 | 6/1996 |
| GB | 1 225 495 | 6/1967 |
| GB | 1 574 267 | 2/1978 |
| GB | 2 109 690 A | 2/1982 |

| | | | |
|---|---|---|---|
| WO | 85/02546 A | 10/1984 |
| WO | 89/08469 A1 | 3/1989 |
| WO | 92/13583 A1 | 2/1992 |
| WO | 93/10838 | 11/1992 |
| WO | 95/03844 A1 | 7/1994 |
| WO | WO 95 29720 A | 11/1995 |
| WO | 96/19252 A1 | 12/1995 |

| | | | |
|---|---|---|---|
| WO | 96/28202 A1 | 3/1996 |
| WO | 97/13537 A1 | 10/1996 |
| WO | 97/25015 A1 | 1/1997 |
| WO | WO 00 48654 A | 8/2000 |

\* cited by examiner

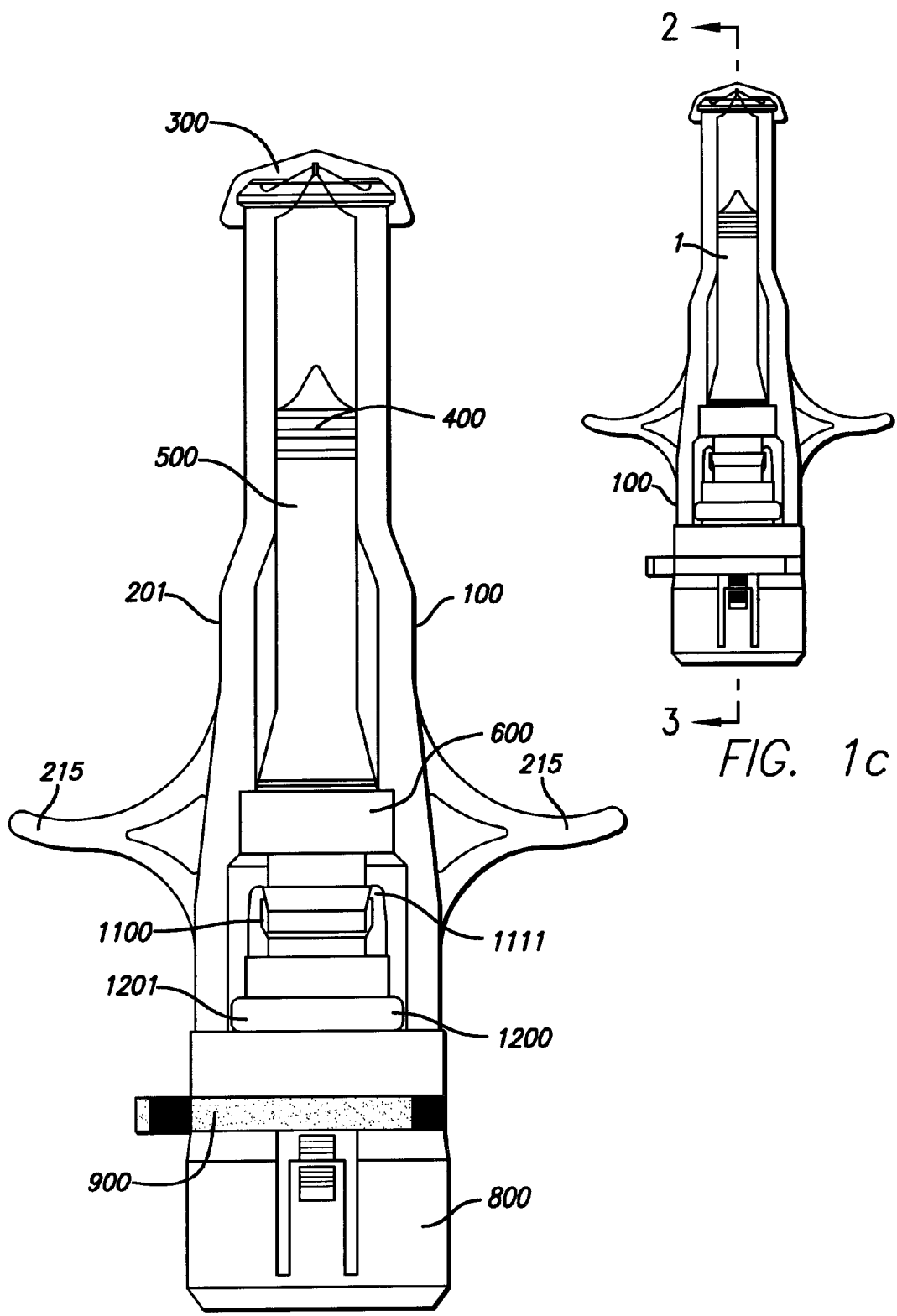

FIG. 15a
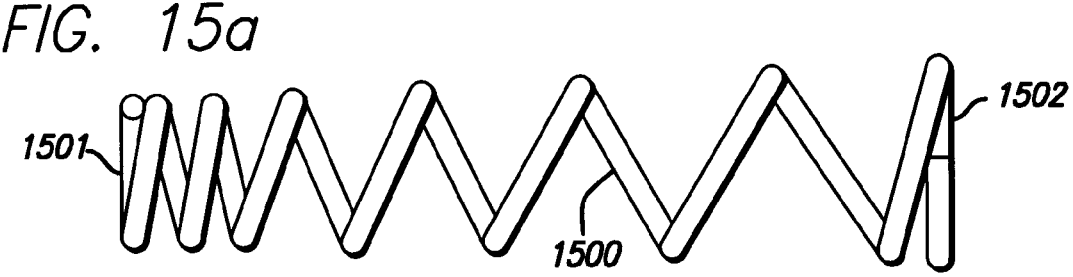
FIG. 15b
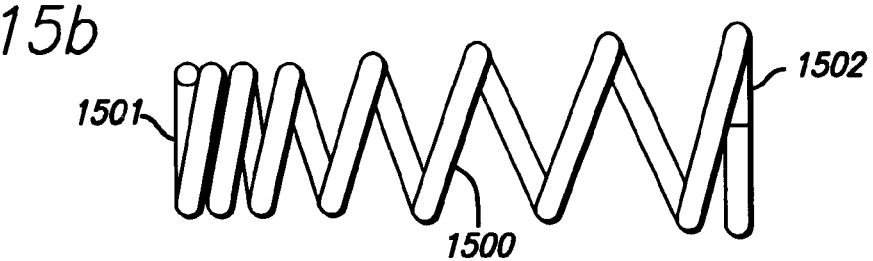
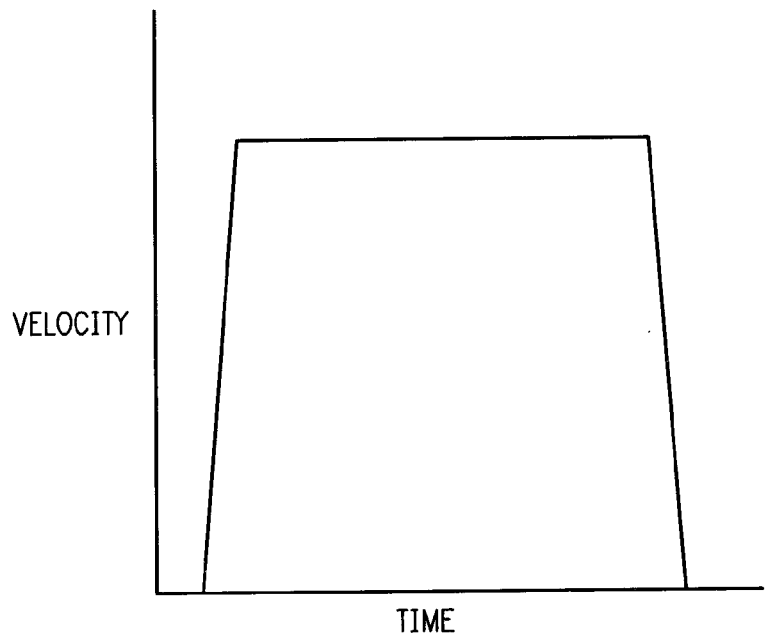
FIG. 16

MODULAR GAS-PRESSURED NEEDLE-LESS INJECTOR

RELATED APPLICATIONS

This application is related to U.S. patent application Ser. No. 09/566,928, filed May 6, 2000. Further, this application generally relates to U.S. patent application Ser. No. 09/215,769, filed Dec. 19, 1998, now U.S. Pat. No. 6,063,053, which is a continuation of U.S. patent application Ser. No. 08/727,911, filed Oct. 9, 1996, now U.S. Pat. No. 5,851,198, which is a continuation-in-part of U.S. patent application Ser. No. 08/719,459, filed Sep. 25, 1996, now U.S. Pat. No. 5,730,723, which is a continuation-in-part of U.S. patent application Ser. No. 08/541,470, filed Oct. 10, 1995, now abandoned. This application is also generally related to U.S. patent application Ser. No. 09/192,079, filed Nov. 14, 1998, now U.S. Pat. No. 6,080,130, and to U.S. patent application Ser. No. 09/808,511, filed Mar. 14, 2001.

FIELD OF THE INVENTION

This invention relates to needle-less injectors, and in particular, modular gas-pressured needle-less injectors and methods of performing needle-less injections using the same.

BACKGROUND OF THE INVENTION

Traditionally, fluids such as medications are injected into patients, either subdermally or intradermally, using hypodermic syringe needles. The body of the syringe is filled with the injectable fluid and, once the needle has pierced the patient's skin, the syringe plunger is depressed so as to expel the injectable fluid out of an opening in the needle. The person performing the injection is usually a trained medical services provider, who manually inserts the hypodermic needle between the layers of a patient's skin for an intradermal injection, or beneath the skin layers for a subcutaneous injection.

Intradermal or subdermal delivery of a medication through the use of a hypodermic needle requires some skill and training for proper and safe administration. In addition, the traditional method of intradermal injections requires actual physical contact and penetration of a needle through the skin surface of the patient, which can be painful for the patient. Traditional needle injectors, such as hypodermic syringes, are also expensive to produce and difficult to use with prepackaged medication doses. Needle injectors also suffer from increased danger of contamination exposure to health care workers administering the injections, and to the general public when such injectors are not properly disposed of.

Jet injectors are generally designed to avoid some or all of these problems. However, not only are conventional jet injectors cumbersome and awkward, but, existing conventional jet injectors are only capable of subcutaneous delivery of a medication beneath the skin layers of a patient. Conventional jet injectors are also somewhat dangerous to use, since they can be discharged without being placed against the skin surface. With a fluid delivery speed of about 800 feet per second (fps) and higher, a conventional jet injector could injure a person's eye at a distance of up to 15 feet. In addition, jet injectors that have not been properly sterilized are notorious for creating infections at the injection site. Moreover, if a jet injector is not positioned properly against the injection site, the injection can result in wetting on the skin surface. Problems associated with improper dosage amounts may arise as well, if some portion of the fluid intended for injection remains on the skin surface following an injection, having not been properly injected into and/or through the skin surface.

Typically, needle-less medication injectors use either an expansion spring or a compressed inert gas to propel the fluid medication (via a push rod plunger) through a small orifice (an injector nozzle) which rests perpendicular to and against the injection site. The fluid medication is generally accelerated at a high rate to a speed of between about 800 feet per second (fps) and 1,200 fps (approximately 244 and 366 meters per second, respectively). This causes the fluid to pierce through the skin surface without the use of a needle, resulting in the medication being deposited in a flower pattern under the skin surface.

It should be noted, however, that compression spring propelled jet injectors do not offer linear delivery speeds (constant speed of the fluid being injected). In addition to this problem, spring propelled jet injectors with weak (e.g., deteriorated) springs often slow fluid delivery speed down while an injection is being administered, resulting in improper fluid penetration. Reduced speed of the fluid can cause improper dosing and bruising at the injection site when the injection surface is the skin of a human recipient.

In a jet injector, if the inert gas is not quickly and properly expelled, fluid may be improperly injected, as with those devices employing a compression spring. Conventional disposable needle-less injectors, such as those shown in U.S. Pat. No. 4,913,699 to Parsons and U.S. Pat. No. 5,009,637 to Newman et al. show a gas-containing, breakable tube that is shattered or cracked open by a side mounted trigger. Difficulties arise in the need to maintain tight tolerances on the breakable member, since minor changes in thickness can dramatically effect the pressure needed to deploy the gas from the gas chamber of the device. In addition, the broken shards of the breakable member are ejected at high speed when the gas is expelled and these shards can occasionally jam between the plunger driver and the housing, thereby preventing proper operation of the needle-less injector. Attempts to prevent small shards from being formed would obviate some of this potential, but tend to make activation of the device more difficult.

U.S. Pat. No. 6,080,130, U.S. Pat. No. 6,063,053, U.S. Pat. No. 5,851,198 and U.S. Pat. No. 5,730,723 describe needle-less injectors incorporating a gas power source, thus obviating some of the limitations inherent in compression spring injectors and addressing many of the concerns of conventional jet injectors. The injectors described therein have a pre-filled and self-contained compressed gas for providing pressure to inject medication into the skin surface of a patient without the use of a needle.

Gas power sources for needle-less injectors that employ either pop valves or breakaway tab valves to release the inert gas stored in their respective gas chambers, however, may only be opened once, thereby presenting difficulty with regard to quality control testing measures. Further, operation of many injectors requires a user to depress a trigger, relying mainly on resistance force from the injection surface to initiate an injection. Where the underlying surface is sensitive, applying such pressure may not be advantageous. Further, if the injection surface is slippery such a device may slide out of place during an injection rendering its use potentially injurious and possibly resulting in improper fluid delivery.

SUMMARY OF THE DISCLOSURE

It is therefore an object of an embodiment of the instant invention to provide gas-pressured needle-less injectors that obviate, for practical purposes, the above-mentioned limitations.

In one embodiment of the instant invention, a needle-less injector suitable for injecting fluid through an injection surface includes a housing, a trigger, an engine, and a driver. The housing contains a fluid and the engine contains a compressed gas. Upon application of a sufficient amount of force to the trigger, the compressed gas is released from the engine forcing the driver through the interior of the housing, expelling the liquid from the housing at a speed sufficient to pierce an injection surface.

In another embodiment of the instant invention, the needle-less injector includes a mechanism for mitigating the kickback associated with releasing compressed gas from the engine. Grips may be included on the engine, mechanically coupling the engine to an element of the needle-less injector that is affixed to the housing, thereby preventing the engine from separating from the housing upon release of compressed gas from the engine. Also, retainer hooks on the interior of the trigger corresponding to latch retainer mechanisms on the exterior of the housing further prevent the engine from separating from the housing.

In yet another embodiment of the instant invention, the housing of the needle-less injector includes finger rests that provide stability in administering an injection and provide resistance to activate the needle-less injector. Thus, a user need not rely solely on resistance from the injection surface to initiate the administration of an injection. The finger rests may be included on opposing sides of the housing, designed to comfortably receive the fingers of a user without substantial slippage.

In yet another embodiment of the instant invention, the engine of the needle-less injector is fitted with a reusable valve. The valve may contain a rubber head that is held against a fixed element of the engine such that depression of the trigger separates the head from the fixed element, releasing the compressed gas from the engine and, further, forcing the driver to expel liquid from the housing. A spring may be included in the valve to help maintain a proper airtight seal with the canister holding the compressed gas.

In yet another embodiment of the instant invention, a safety clamp is included on the exterior of the housing of the needle-less injector, preventing accidental activation of the device. The safety clamp must be removed prior to use and may be made of a sufficiently elastic material such that a user need only deform the clamp, aided by grips included thereon, to remove the clamp from the housing.

BRIEF DESCRIPTION OF THE DRAWINGS

FIGS. 1a–1e illustrate a needle-less injector in accordance with an embodiment of the instant invention. FIG. 1a is a side perspective view prior to administration of an injection, shown at 0° rotation about the central axis of the injector, FIG. 1b is a side cross-sectional view, the injector having been rotated 90° about the central axis, FIG. 1c is a side perspective view at 0° rotation about the central axis, FIG. 1d is a side perspective view after administration of an injection, shown at 180° rotation about the central axis of the injector and FIG. 1e is a side partial cross-sectional view after administration of an injection, the injector having been rotated 90° about the central axis.

FIG. 2a is a side perspective view at 180° rotation about the central axis of the injector, FIG. 2b is a proximate end perspective view and FIG. 2c is a distal end perspective view.

FIG. 3a is a side perspective view, FIG. 3b is a side cross-sectional view and FIG. 3c is a proximate end perspective view.

FIG. 4a is a side perspective view, FIG. 4b is a side cross-sectional view and FIG. 4c is a proximate end perspective view.

FIG. 5a is a side perspective view, FIG. 5b is a side cross-sectional view, FIG. 5c is a proximate end perspective view and FIG. 5d is a distal end perspective view.

FIG. 6a is a side perspective view, FIG. 6b is a side cross-sectional view, FIG. 6c is a proximate end perspective view and FIG. 6d is a distal end perspective view.

FIG. 8a is a side perspective view at 0° rotation about the central axis of the trigger, FIG. 8b is a side cross-sectional view at 90° rotation, FIG. 8c is a proximate end perspective view and FIG. 8d is a distal end perspective view.

FIG. 9a is a proximate end perspective view and FIG. 9b is a side perspective view.

FIG. 10a is a side perspective view, FIG. 10b is a side cross-sectional view, FIG. 10c is a proximate end perspective view and FIG. 10d is a distal end perspective view.

FIG. 11a is a side perspective view, FIG. 11b is a side cross-sectional view and FIG. 11c is a proximate end perspective view.

FIG. 12a is a side perspective view, FIG. 12b is a side cross-sectional view and FIG. 12c is a proximate end perspective view.

FIG. 13a is a side perspective view in partial cross-section, FIG. 13b is a side cross-sectional view, FIG. 13c is a proximate end perspective view and FIG. 13d is a distal end perspective view.

FIG. 14a is a side perspective view, FIG. 14b is a side cross-sectional view prior to the distal end being shaped and FIG. 14c is a proximate end perspective view.

FIGS. 15a–b illustrate the valve spring of a needle-less injector in accordance with an embodiment of the instant invention. FIG. 15a is a side perspective view in the relaxed state, FIG. 15b is a side perspective view in the compressed state.

FIG. 16 is a graph depicting the velocity of the driver of an embodiment of the instant invention during administration of an injection.

DETAILED DESCRIPTION OF THE PREFERRED EMBODIMENTS

Figure 1B:
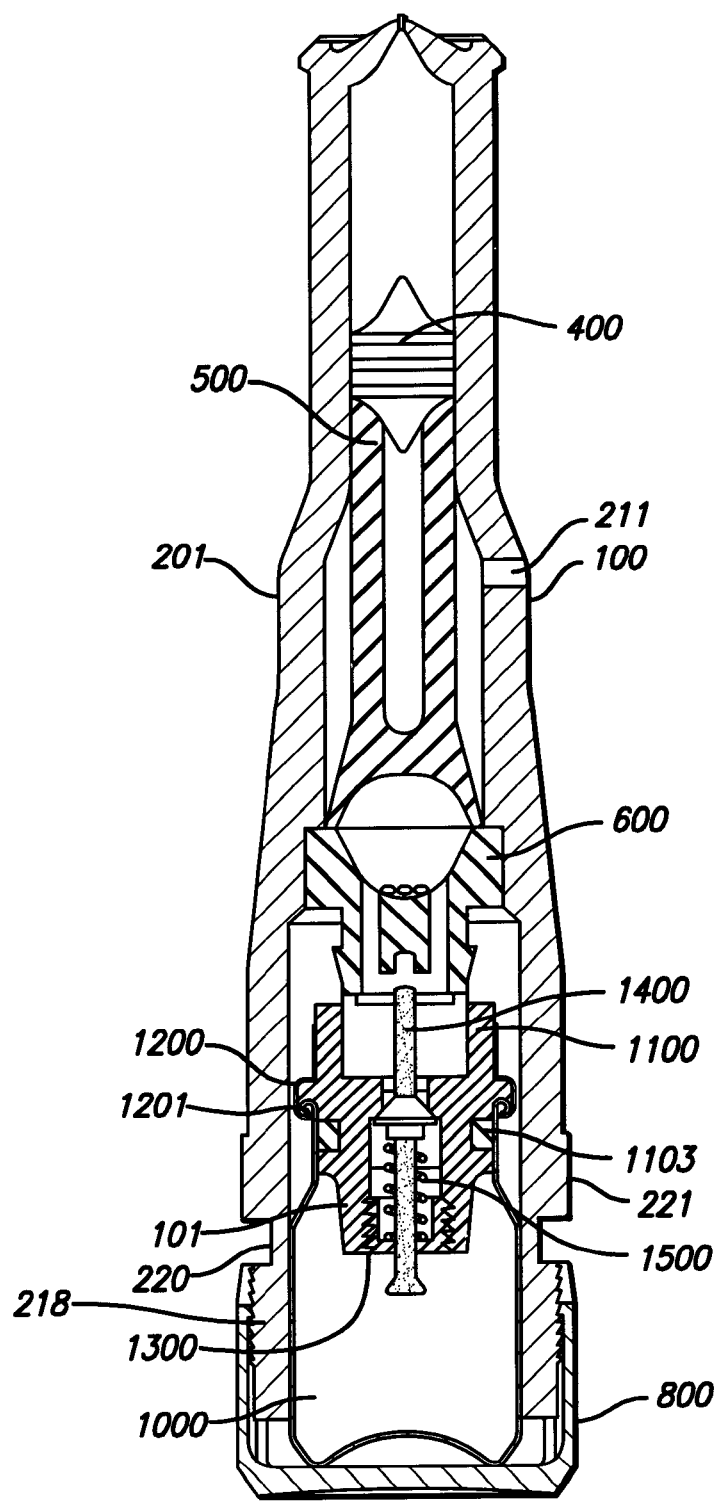

As shown in the drawings for purposes of illustration, the invention is embodied in a gas-pressured needle-less injector. In preferred embodiments of the present invention, the gas-pressured needle-less injector is pre-loaded with medication and is adapted for a single use. Preferably, the needle-less injector is for use with human beings or other animals. However, it will be recognized that further embodiments of the invention may be used in other applications requiring needle-less injection, such as passing injectable materials through a porous membrane or the like.

Also, embodiments of the present invention may be used to inject other fluids or injectants such as proteins, vitamins, hormones, drugs, vaccines, medications, lyophilized medications, medication cocktails, or the like, and such are contemplated as being within the scope of the term "liquid" as used herein. In preferred embodiments, the liquids used in accordance with the present invention are de-gassed prior to filling into the needle-less injector or are of sufficient chemical properties such that the liquids de-gas immediately upon or soon after filling, as described in U.S. patent application Ser. No. 09/808,511, filed Mar. 14, 2001. In either of such preferred embodiments, substantially no gas pocket develops in the interior cavity where the liquid resides during storage of the needle-less injector, prior to use.

For ease in describing the various elements of the instant invention, the following spatial coordinate system will apply thereto. As depicted in FIG. 1c, a central axis is defined through the length of a gas-pressured needle-less injector 100. This central axis 1 has one terminus at the proximate end 2 of the needle-less injector 100, defined as that end of the device in contact with an injection surface during normal operation of the injector. The other terminus of the central axis is at the distal end 3 of the injector 100, defined as that end of the device furthest from the injection surface when the injector is positioned perpendicular to the injection surface. Thus, various elements of the device of the instant invention may be described with reference to their respective proximate and distal portions, as well as their central axes.

As depicted in FIG. 1, a gas-pressured needle-less injector 100 includes a housing 201. The housing 201 may be of any suitable shape, though in preferred embodiments it is roughly cylindrical about the central axis. The housing 201 preferably has a varying interior diameter along its length to accommodate the elements that reside and operate therein when the injector 100 is fully assembled. The housing 201 depicted in FIG. 2a has four such interior diameters: an ampoule diameter 202, a piston diameter 203, a diffuser diameter 204 and an engine diameter 205, respectively. Embodiments of the instant invention preferably do not have an ampoule that is a mechanical element separate and distinct from the housing 201, yet the housing 201 may act as an ampoule for various purposes such as filling with liquid.

The exterior portion 206 of the proximate end surface of the housing 201 may be flat, though in preferred embodiments it is of a shape that maximizes injector efficacy. Efficacy is optimal when substantially all liquid contained in the injector 100 is delivered through the injection surface, leaving substantially no liquid on either the injection surface or the exterior portion 206 of the proximate end surface of the housing 201 after an injection is complete (see FIGS. 1d and 1e). To that end, in the embodiment depicted in FIG. 2a, the exterior portion 206 of the proximate end of the housing 201 is adapted to pinch and stretch the surface through which an injection is to be administered, as the exterior portion 206 of the proximate end surface of the housing 201 is brought into contact with an injection surface. Thus, the exterior portion 206 of the proximate end of the housing 201 preferably has a conical shape about the central axis, and further possesses an elevated rim 207 around its circumference.

Figure 1D:
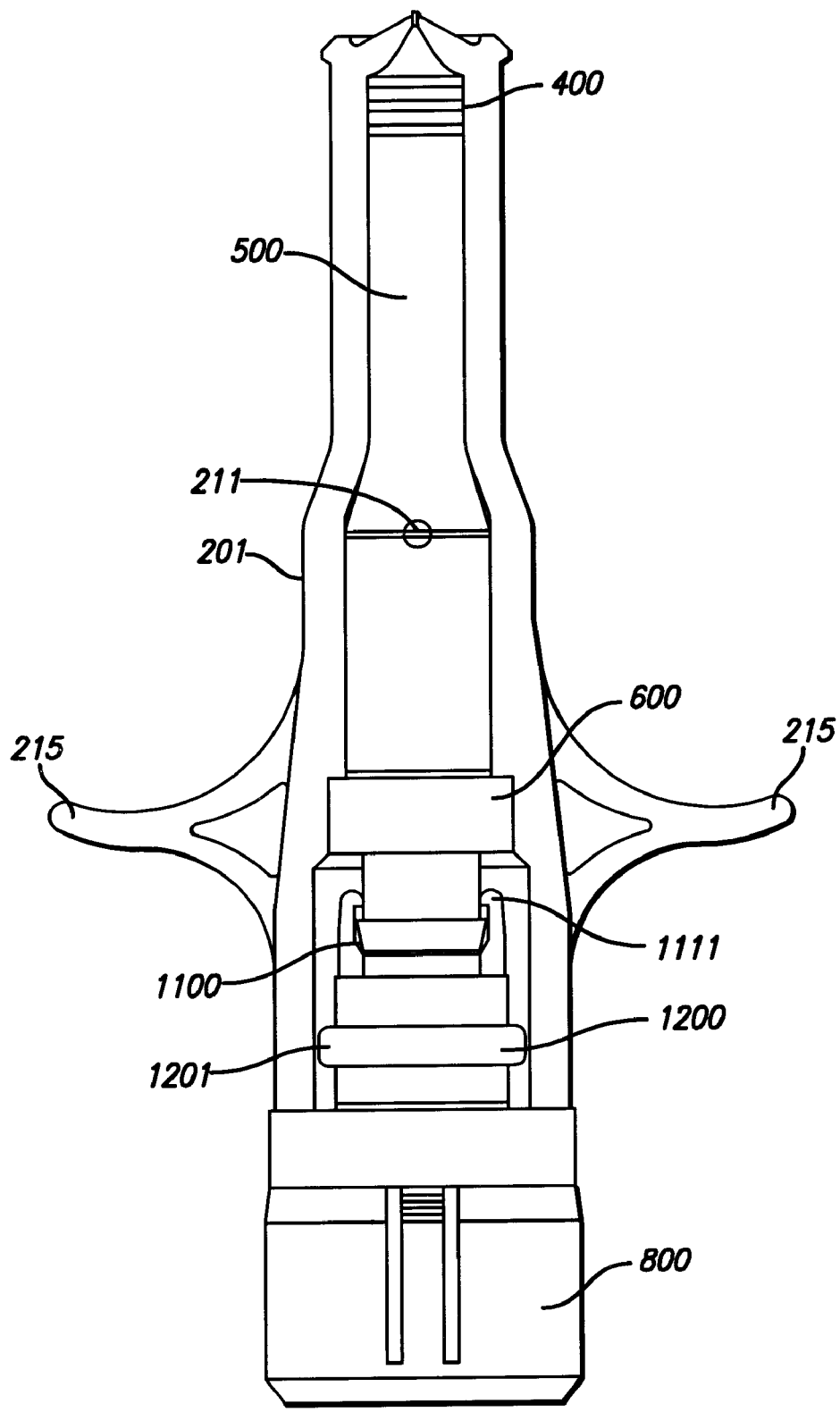
Figure 1E:
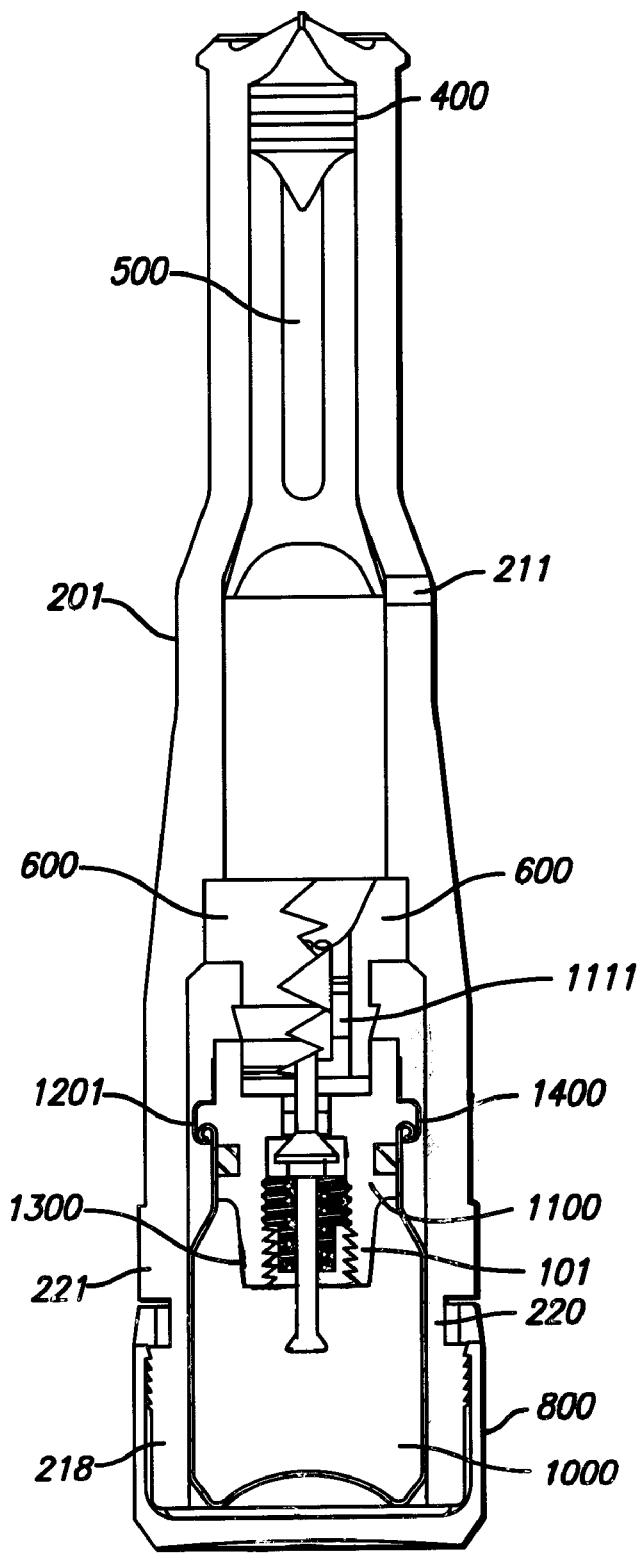
Figure 2A:
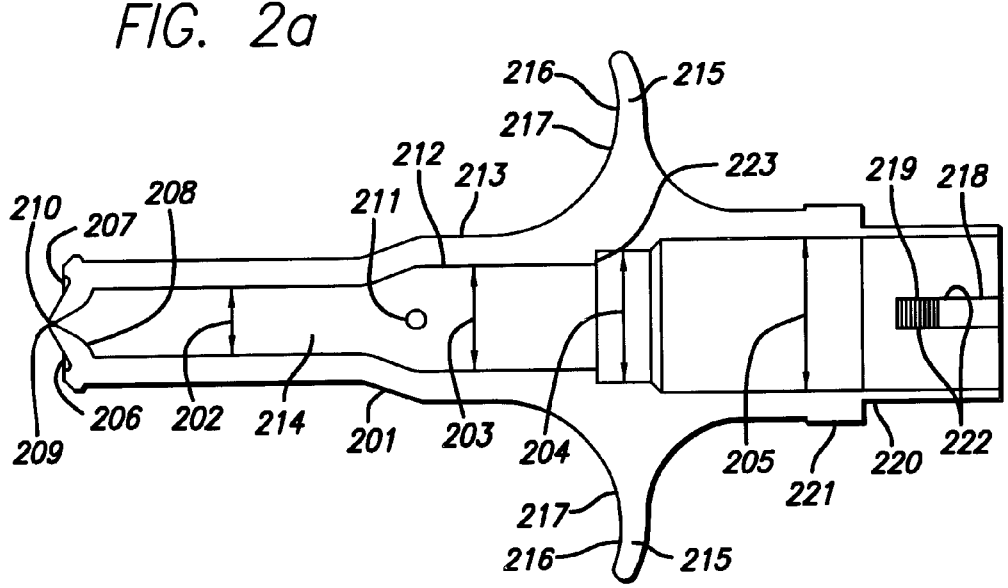
FIGS. 2a–2c illustrate the housing of a needle-less injector in accordance with an embodiment of the instant invention.
Figure 2B:
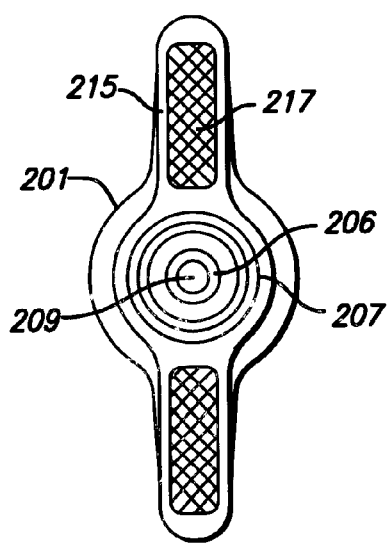
Figure 2C:
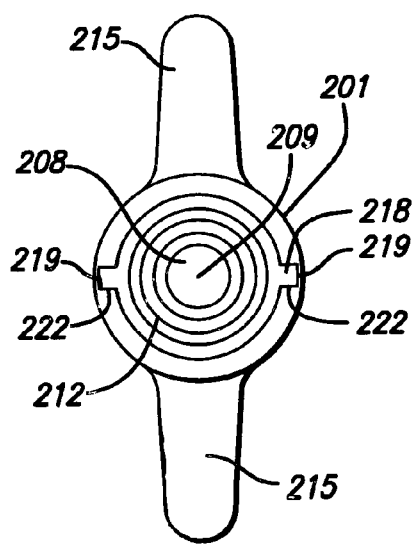

The interior portion 208 of the proximate end of the housing 201 may be of any appropriate shape. It may conform roughly to the shape of the exterior portion 207, or have a design independent thereof. In one embodiment, the interior portion 208 is flat, though preferably, as depicted in FIG. 2a the interior portion 208 is roughly conical, with at least one orifice 209 at or near the vertex 210. The needle-less injector 100 depicted in FIG. 1 is shown with only one orifice.

The at least one orifice 209 provides fluid communication between the interior 214 of the housing 201 and the surface through which an injection is administered. The number of orifices 209 may be varied depending on the delivery parameters of the liquid to be injected. One such parameter is the depth to which a liquid must penetrate a recipient's tissue, when the device is used for the injection of a medicament into a human being. For example, in one embodiment it may be desirable to inject a liquid just beneath the outermost skin layers of a recipient, and multiple orifices may best suit that end. Alternatively, a single orifice may be most desirable for an injection that requires deeper penetration for maximum drug efficacy.

An exhaust passage 211 may be created through the housing 201, from the interior wall 212 to the exterior wall 213, preferably within the section of the housing 201 of ampoule diameter 202. The exhaust passage 211 allows gas to vent from the interior 214 of the housing 201 preferably only after an injection has been administered. Thus, most preferably, the exhaust passage 211 is located at a point in the housing 201 at or immediately distal to the location of the piston 500 (see FIGS. 1d and 1e) after administration of an injection. In these most preferred embodiments, gas may not vent from the interior 214 of the housing 201 through the exhaust passage 211 until after substantially all liquid contained in the housing 201 has been discharged from the needle-less injector 100, with the piston 500 at rest in its final position.

Liquid stored in the needle-less injector 100, prior to administration of an injection, is preferably contained in the interior 214 of the housing 201 in the region bounded by the interior portion 208 of the proximate end of the housing 201, the interior wall 212 of the housing 201 and the proximate end 403 of the plunger 400 (see FIGS. 1a and 2a).

As depicted in FIG. 2a, the housing 201 may further include finger rests 215. In preferred embodiments, two such finger rests 215 are formed on the exterior wall 213 of the housing 201 at opposing locations. Most preferably, the finger rests 215 are located directly opposite one another. In preferred embodiments, each finger rest 215 has an arc 216 on the proximate side thereof to accommodate proper finger placement for either self-administration of an injection or assisted administration by a health care professional or the like. In the most preferred embodiments, the arcs 216 of the finger rests 215 further contain a non-slip, textured surface 217.

When the needle-less injector 100 is used by an individual performing self-administration of an injection, the individual's thumb and middle finger may be placed in the arcs 216 of the finger rests 215 on opposing sides of the housing 201 for stabilization of the device, with the index finger operably placed against the trigger 800 at the distal end of the injector 100. Another manner in which a user may perform self-administration of an injection, which is also the manner preferred when the needle-less injector 100 is operated by an individual other than the recipient of an injection, involves the index and middle fingers being placed in the arcs 216 of the finger rests 215 on opposing sides of the housing 201 for stabilization of the device, with the thumb operably placed against the trigger 800 at the distal end of the injector 100.

The housing 201 may further contain at least one latch retainer mechanism 218 near the distal end. The at least one latch retainer mechanism 218 may be comprised of a single set of saw tooth ridges that encircle the exterior wall 213 of the housing 201 around its central axis. More preferably, there are two latch retainer mechanisms 218 comprising two sets of saw tooth ridges 219, disposed opposite one another on the exterior wall 213 of the housing 201, though any appropriate number of latch retainer mechanisms 218 may be utilized. Preferably, as shown in FIG. 1b, the housing 201 further contains a clamp indentation 220 that is defined on its proximate end by a ridge 221 and on its distal end by the at least one latch retainer mechanism 218 and the proximate end of the trigger 800.

Figure 3A:
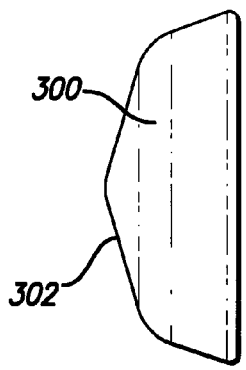
FIGS. 3a–c illustrate the ampoule cap of a needle-less injector in accordance with an embodiment of the instant invention.
Figure 3B:
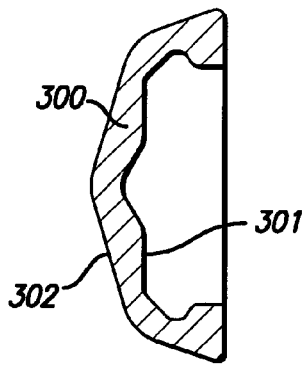
Figure 3C:
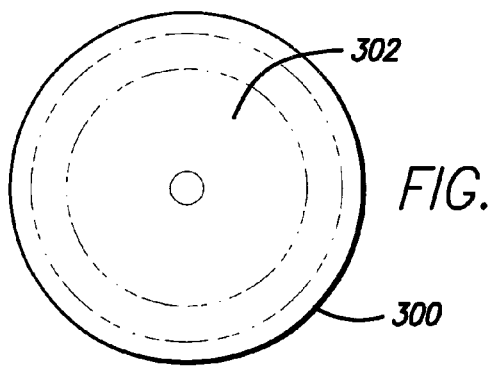

The proximate end of the housing 201 may further be fit with an ampoule cap 300, as depicted in FIG. 3, which serves to maintain sterility of the exterior portion 206 of the proximate end surface of the housing 201 while the needle-less injector 100 is stored. Further, when de-gassed liquids are used in accordance with the present invention, the ampoule cap 300 provides the requisite airtight seal between the at least one orifice 209 in the proximate end of the housing 201 and the local atmosphere, such that the de-gassed liquids may remain gas-free during storage. Referring again to FIG. 3, the interior 301 of the ampoule cap 300 is preferably designed to conform substantially to the exterior surface 206 of the proximate end of the housing 201, while the exterior 302 of the ampoule cap 300 may be of any convenient configuration.

Figure 4A:
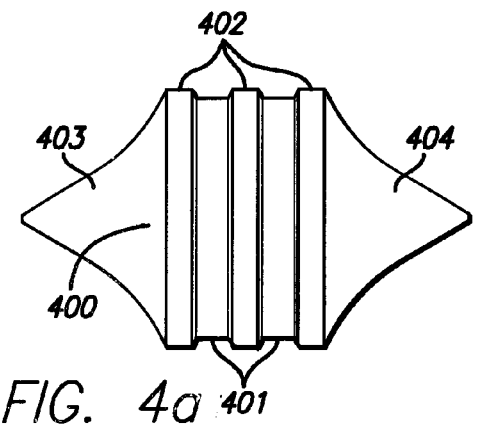
FIGS. 4a–c illustrate the plunger of a needle-less injector in accordance with an embodiment of the instant invention.
Figure 4B:
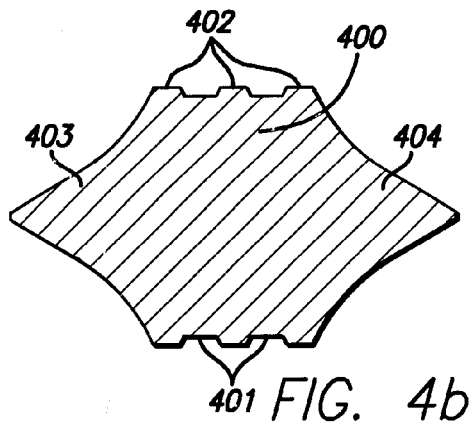
Figure 4C:
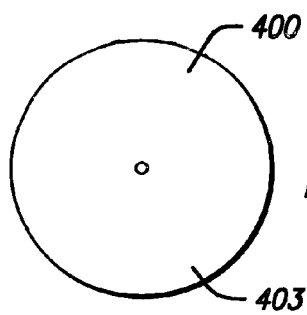
Figure 5A:
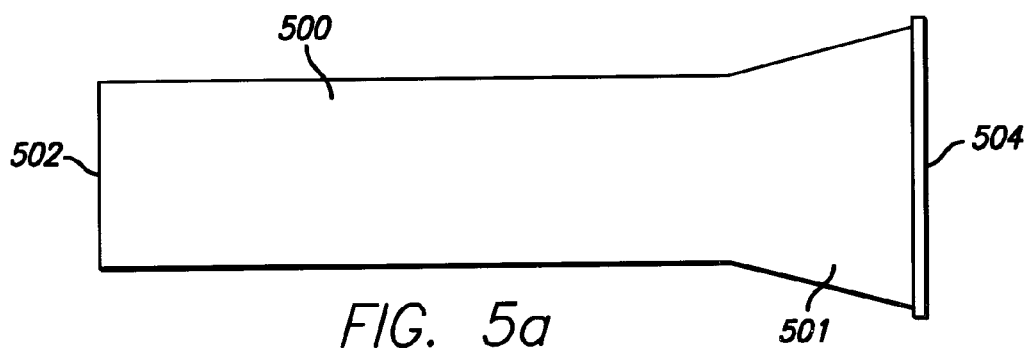
FIGS. 5a–d illustrate the piston of a needle-less injector in accordance with an embodiment of the instant invention.
Figure 5B:
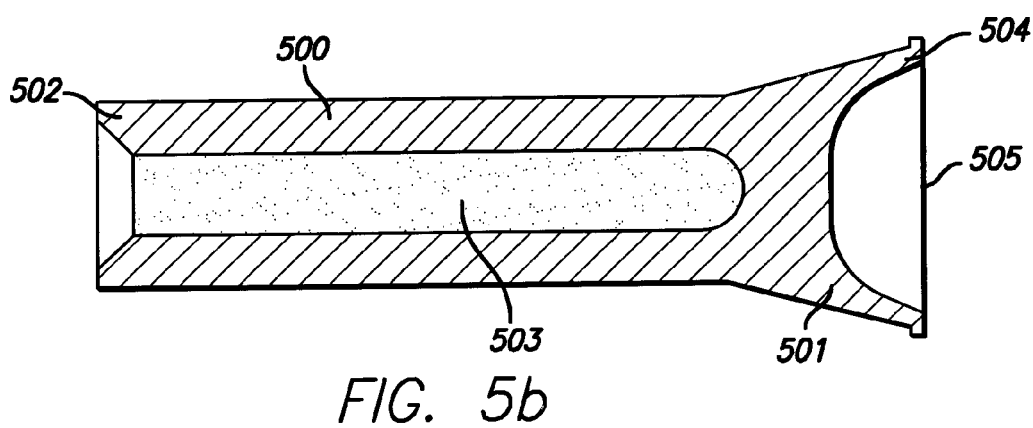
Figure 5C:
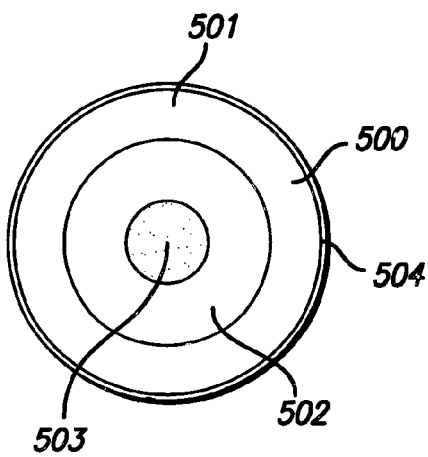
Figure 5D:
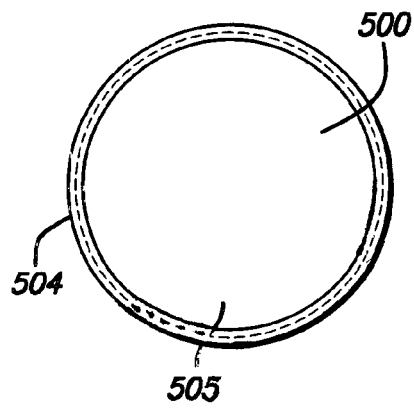

As depicted in FIG. 4, the housing 201 may be fit with a plunger 400. Preferably, the plunger 400 is pressure-fit within the housing 201, as its diameter is equivalent to or slightly greater than the ampoule diameter 202 of the housing 201. The plunger 400 is preferably constructed of a sufficiently elastic material such that the pressure-fit creates an air and liquidtight seal with the interior wall 212 of the housing 201. The plunger 400 is preferably cylindrical to mirror the shape of the interior wall 212 of the housing 201, though other shapes may be suitable especially where the interior wall 212 of the housing 201 is not cylindrical. Moreover, the wall 401 of the plunger 400 may have multiple ridges 402 disposed thereupon. Preferably, there are at least two such ridges 402, and most preferably there are three ridges 402. These ridges 402 provide stability to the plunger 400 such that its direction of travel during administration of an injection remains substantially linear along the central axis, without rotational motion around any axis other than the central axis.

The proximate end 403 of the plunger 400 may be of any suitable shape, including a flat surface, though in preferred embodiments it roughly mirrors the shape of the interior wall 208 of the proximate end of the housing 201. However, the elastic properties of the plunger material may allow the proximate end 403 of the plunger 400 to conform to the shape of a surface different than its own when mechanically forced against such a surface. Thus, the shape of the proximate end 403 of the plunger 400 need not mirror the shape of the interior wall 208 of the proximate end of the housing 201, yet the plunger proximate end 403 may conform to the shape of the interior wall 208 when forced against it during or after an injection is administered. In most preferred embodiments, however, the proximate end 403 of the plunger 400 is roughly conical in shape.

The distal end 404 of the plunger 400 may similarly be of any suitable shape, and is received by the proximate end of the piston 500. In preferred embodiments, the plunger 400 is symmetrical in shape along a plane perpendicular to the central axis. Thus, in preferred embodiments, the distal end 404 of the plunger 400 is roughly conical in shape.

The housing 201 may be fit with a piston 500, as depicted in FIG. 5. The piston 500 preferably is of roughly cylindrical shape along the length of its central axis with a flared portion 501 toward its distal end, though other shapes may be appropriate especially in those embodiments where the interior wall 212 of the housing 201 is non-cylindrical. Preferably, the proximate end 502 of the piston 500 is shaped such that it mechanically receives the distal end 404 of the plunger 400. Thus, in most preferred embodiments, the proximate end 502 of the piston 500 is a roughly conical indentation. In preferred embodiments, the piston 500 further includes a chamber 503 that extends from the vertex of the conical indentation 502 along the central axis of the piston 500.

The exterior of the distal section of the piston is preferably a flared portion 501, terminating in an expansion cup rim 504. In most preferred embodiments, the distal section of the piston further has a hollow expansion cup 505. This expansion cup 505 is not in gaseous communication with the chamber 503 that extends from the proximate end 502 of the piston 500 along the piston central axis, as the chamber 503 does not extend entirely through the piston 500 to the expansion cup 505.

Referring to FIGS. 2a and 5, the distal section of the piston 500 may be pressure-fit within the portion of the housing 201 of piston diameter 203, such that the diameter of the expansion cup rim 504 of the piston 500 is substantially equivalent to the piston diameter 203 of the housing 201. Alternatively, the diameter of the expansion cup rim 504 may be slightly less than the piston diameter 203 of the housing 201. During use of the needle-less injector 100, the expansion cup 505 may expand radially due to the force of compressed gas pushing upon it. This serves to optimize the performance of the piston 500, as a substantially airtight seal is thus formed between the expansion cup rim 504 and the interior wall 212 of the housing 201.

The housing 201 may be fit with a diffuser 600, as depicted in FIG. 6. The diffuser 600 is preferably affixed to the housing 201 along the interior wall 212 thereof at the portion of diffuser diameter 204. Affixing may be performed by high frequency welding or other suitable means. Most preferably, the diffuser 600 is affixed to the housing 201 only after the plunger 400 and piston 500 have been fit within the housing 201.

The diffuser 600 preferably further contains at least one channel 601 that provides gaseous communication between the distal end 602 of the diffuser 600 and the base of the diffuser cup 603. The at least one channel 601 is sized and positioned to optimize the injection delivery parameters of a particular liquid. In preferred embodiments, as illustratively depicted in FIG. 7, the diffuser 600 may contain between two and eight channels 601, which may be of the same or different diameter, and may be symmetrically or nonsymmetrically oriented about the central axis of the diffuser 600. Selection of various combinations of channels 601 in the diffuser 600 will affect the delivery performance of the needle-less injector 100, altering, for example, the initial acceleration of the driver of the needle-less injector 100. The velocity of the driver of the preferred embodiment of the instant invention is depicted in FIG. 16. Notably, the compressed gas engine of the instant invention allows for a substantially constant delivery velocity during the bulk of the injection.

Figure 6A:
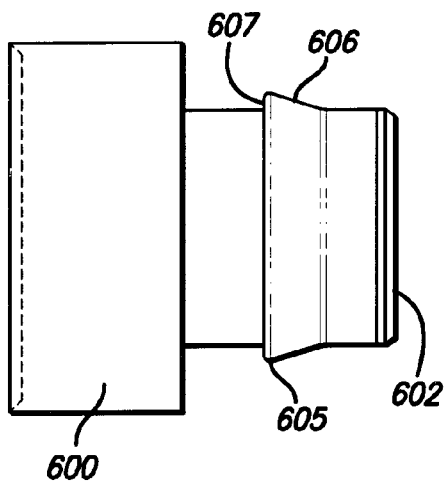
FIGS. 6a–d illustrate the diffuser of a needle-less injector in accordance with an embodiment of the instant invention.
Figure 6B:
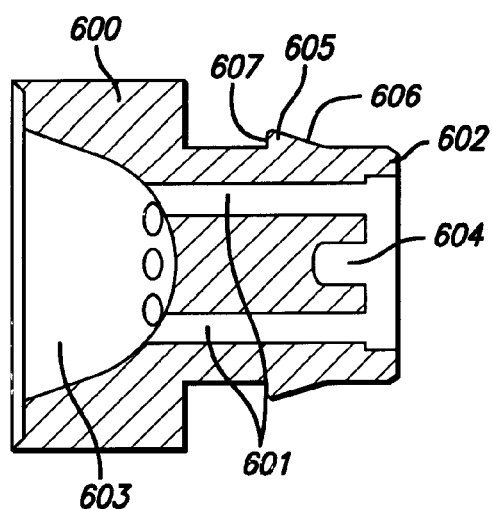
Figure 6C:
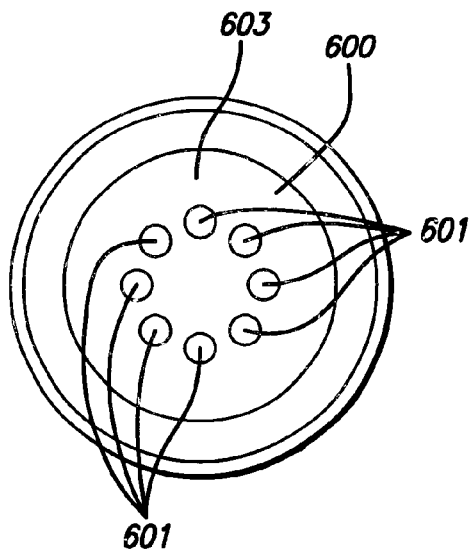
Figure 6D:
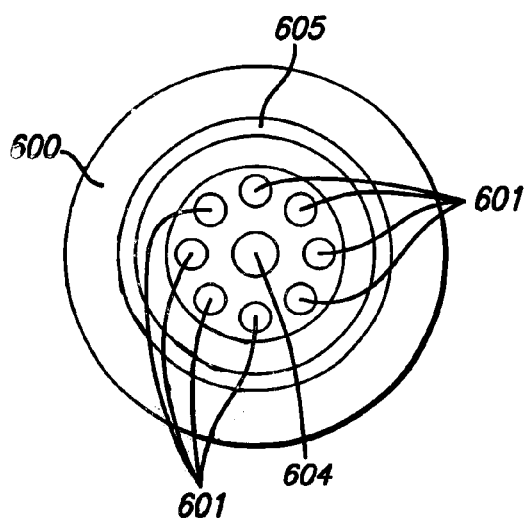
Figure 7A:
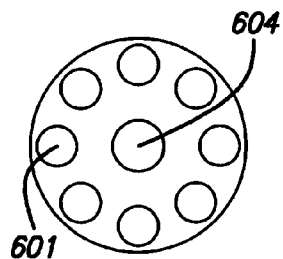
FIGS. 7a–i illustrate various configurations of channels in the diffuser of a needle-less injector in accordance with embodiments of the instant invention.
Figure 7B:
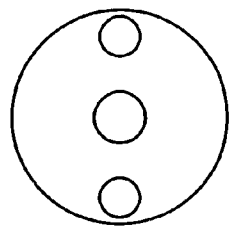
Figure 7C:
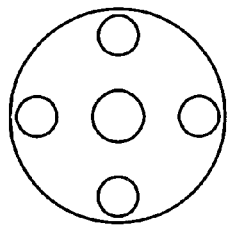
Figure 7D:
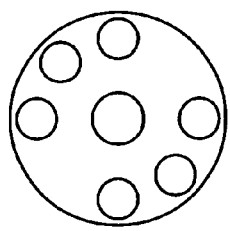
Figure 7E:
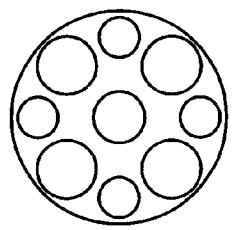
Figure 7F:
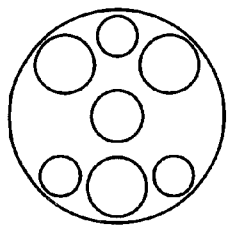
Figure 7G:
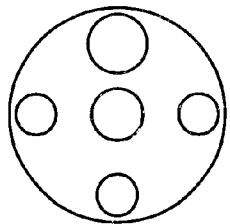
Figure 7H:
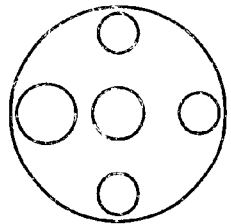
Figure 7I:
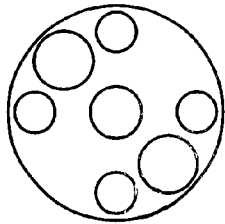
Figure 8A:
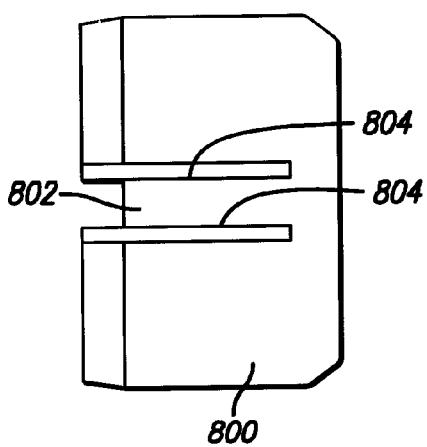
FIGS. 8a–d illustrate the trigger of a needle-less injector in accordance with an embodiment of the instant invention.
Figure 8B:
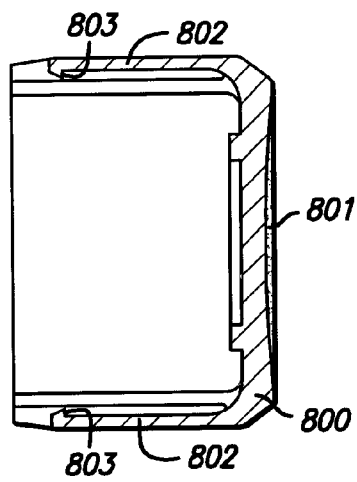
Figure 8C:
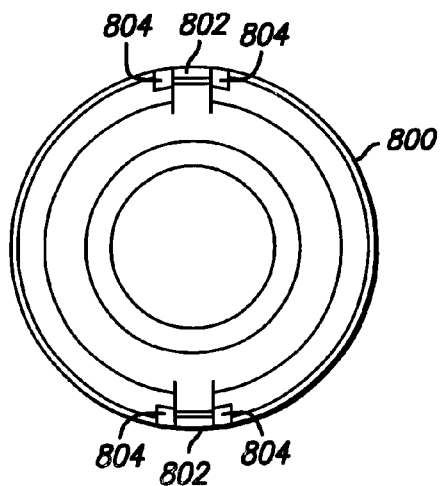
Figure 8D:
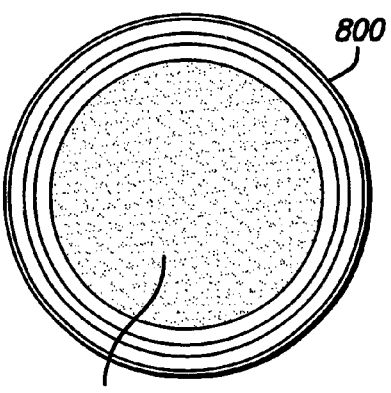

Referring to FIG. 6b, a valve stem support depression 604 may further be included on the distal end 602 of the diffuser 600, located at the diffuser central axis. The diffuser 600 may further contain a locking ring 605 around its outer circumference. Preferably the locking ring 605 is angled on its distal surface 606, but is flat on its proximate surface 607.

The housing 201 may further be fit with a trigger 800, as depicted in FIG. 8. The trigger 800 is preferably roughly cylindrical, to match the shape of the exterior wall 213 of the housing 201. The distal end of the trigger 800 may have a depression 801 therein, and in preferred embodiments this depression 801 may further be textured for non-slip finger placement during operation of the needle-less injector 100.

The trigger 800 preferably contains at least one retainer hook mechanism 802 used both for securing the trigger 800 to the housing 201 and for mitigating the kickback associated with deploying the compressed gas stored in the engine housing 1000. Without such a safety feature, the force created by release of gas stored in the engine housing 1000 may cause the engine assembly to separate from the remainder of the needle-less injector 100, potentially resulting in both an improper injection and injury to the user.

The at least one retainer hook mechanism 802 operably mates with the at least one latch retainer mechanism 218 located near the distal end of the housing 201 as the retainer hook 803 at the proximate end of the retainer hook mechanism 802 locks around consecutive saw tooth ridges 219 that preferably comprise the latch retainer mechanism 218. In preferred embodiments, there are two retainer hook mechanisms 802, located opposite one another on the trigger 800, that spatially correspond to two latch retainer mechanisms 218 on the exterior wall 213 of the housing 201.

The at least one retainer hook mechanism 802 and at least one latch retainer mechanism 218 preferably prevent the trigger 800 from rotating about its central axis. In a most preferred embodiment, the sides 804 of the at least one retainer hook mechanism 802 fit around the sides 222 of the at least one latch retainer mechanism 218, preventing such rotation.

Figure 9A:
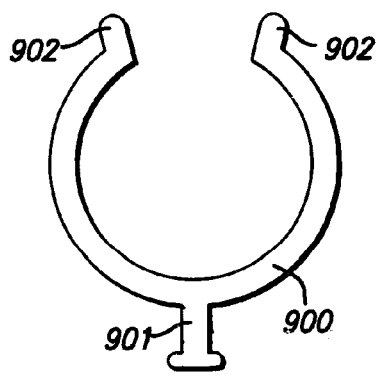
FIGS. 9a–b illustrate the safety clamp of a needle-less injector in accordance with an embodiment of the instant invention.
Figure 9B:
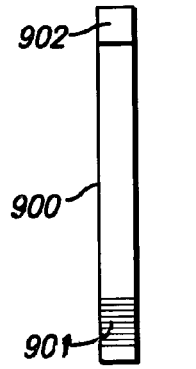
Figure 10A:
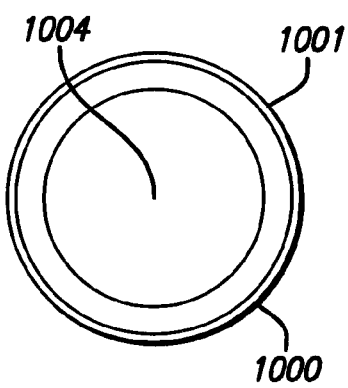
FIGS. 10a–d illustrate the engine housing of a needle-less injector in accordance with an embodiment of the instant invention.
Figure 10B:
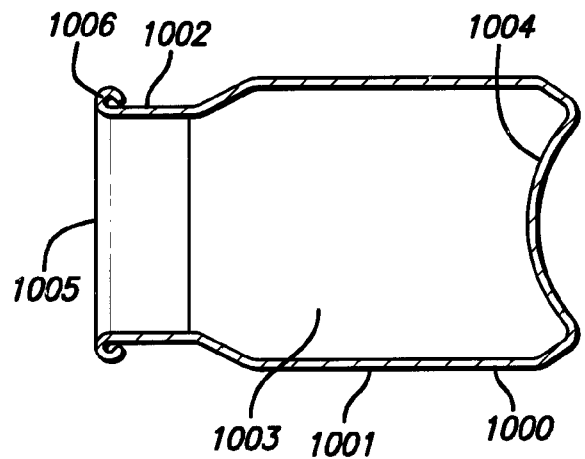
Figure 10C:
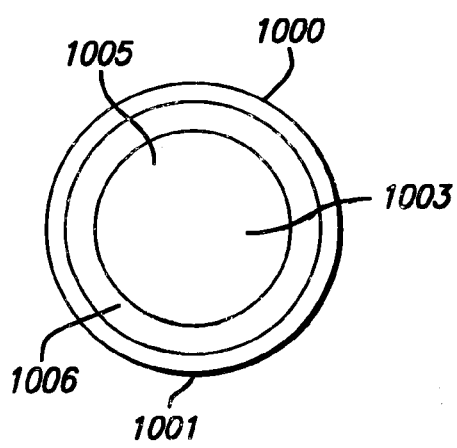
Figure 10D:
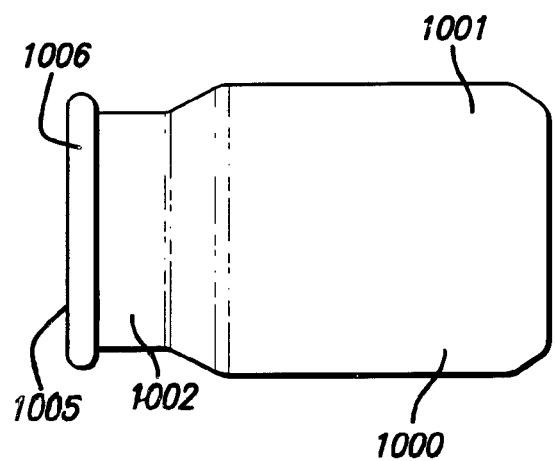

The housing 201 may further be fit with a safety clamp 900, as depicted in FIG. 9. The safety clamp 900 prevents the needle-less injector 100 from being discharged accidentally. The safety clamp 900 is preferably roughly semi-cylindrical in shape to conform to the exterior wall 213 of the housing 201, and resides around the exterior wall 213 of the housing 201 in the clamp indentation 220 that is defined on its proximate end by a ridge 221 and on its distal end by the at least one latch retainer mechanism 218 and the proximate end of the trigger 800 (see FIG. 1b). The safety clamp 900 preferably does not completely encircle the housing 201, but rather encircles only at least half of the housing 201, allowing for easy removal while preventing the clamp 900 from simply falling off of the injector 100. Most preferably, the safety clamp 900 is constructed of a sufficiently elastic material such that temporarily deforming the clamp 900 permits removal thereof from the exterior wall 213 of the housing 201. To aid in this removal, a grip 901 and feet 902 may be included on the safety clamp 900.

The housing 201 is preferably fit with an engine assembly 101, as depicted in FIG. 1b. The engine assembly 101 may further contain an engine housing 1000, as depicted in FIG. 10. The engine housing 1000 is preferably constructed of a material impermeable to a compressed gas stored therein, and has a hollow interior chamber 1003. Most preferably, the engine housing 1000 is comprised of stainless steel or a similar metal. A compressed inert gas is preferably used to drive the needle-less injector 100 and is stored within the engine housing 1000 prior to use. The most preferred gas is carbon dioxide, though other suitable gases may be employed, as well. In most preferred embodiments, the engine assembly 101 is overcharged (i.e., excess compressed gas is stored therein) to allow for use at variable altitudes without hampering the performance characteristics of the needle-less injector 100.

The engine housing 1000 is preferably roughly cylindrical in shape to match the interior wall 212 of the housing 201, though alternate configurations may be utilized. Referring to FIG. 10, the engine housing 1000 may have a portion of wide diameter 1001 and a portion of small diameter 1002, wherein the portion of small diameter 1002 is proximate to the portion of wide diameter 1001. The distal end of the engine housing 1000 may contain a circular depression 1004 and may rest against the trigger 800 (see FIG. 1b). The proximate end of the engine housing 1000 contains an opening 1005, and in preferred embodiments, a closing ridge 1006 encircles the opening 1005.

Figure 11A:
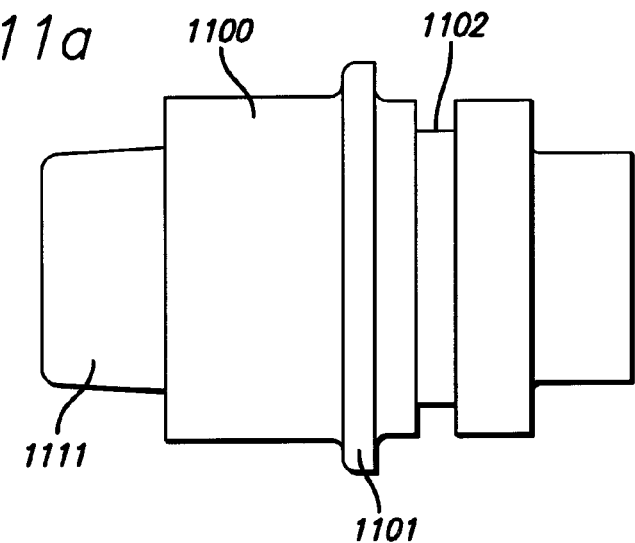
FIGS. 11a–c illustrate the valve body of a needle-less injector in accordance with an embodiment of the instant invention.
Figure 11B:
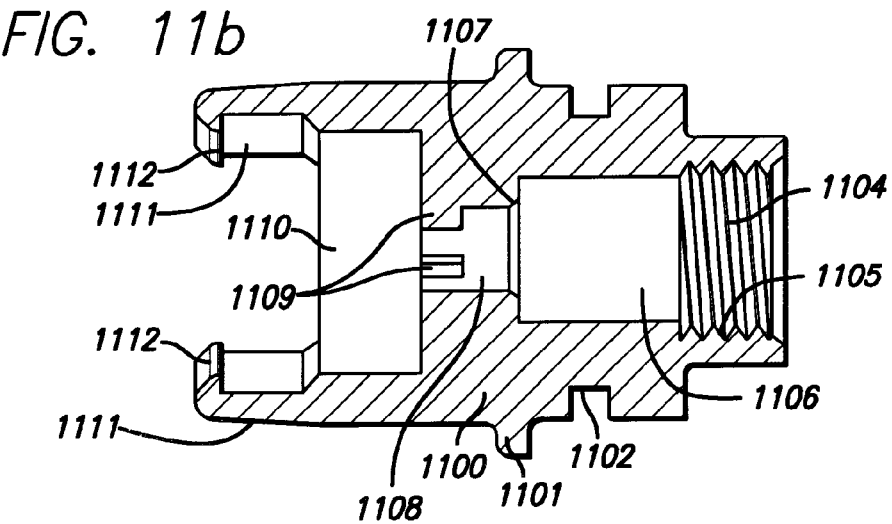
Figure 11C:
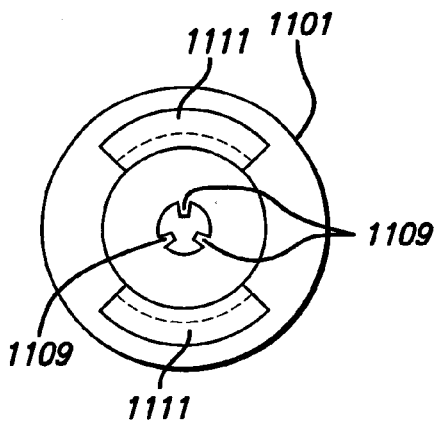

The engine assembly 101 preferably further contains a valve body 1100, as depicted in FIG. 11. The valve body 1100 is preferably roughly cylindrical in its overall shape, and more preferably resides at least partially within the engine housing 1000. The valve body 1100 most preferably has a closing rim 1101 around its outer circumference that rests against the closing ridge 1006 encircling the opening 1005 of the proximate end of the engine housing 1000. Most preferably, a closing ferrule 1200 is wrapped around both the closing rim 1101 and closing ridge 1006 to secure the valve body 1100 and engine housing 1000 to one another (see FIG. 1b).

Figure 12A:
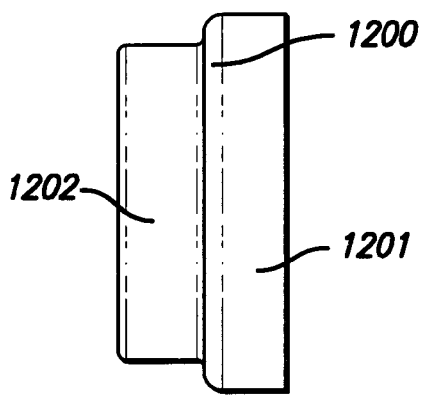
FIGS. 12a–c illustrate the closing ferrule of a needle-less injector in accordance with an embodiment of the instant invention, prior to the closing ferrule being mechanically fitted around a valve body and an engine housing.
Figure 12B:
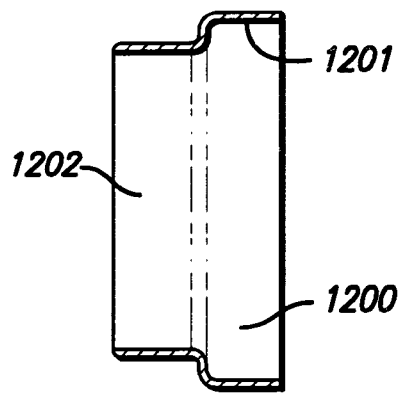
Figure 12C:
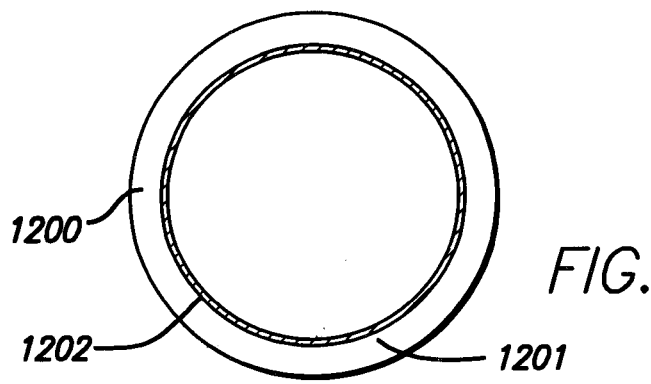
Figure 13A:
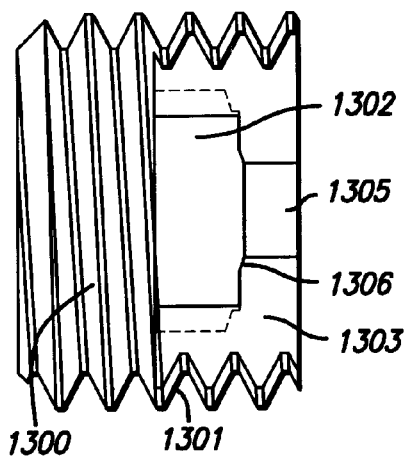
FIGS. 13a–d illustrate the threaded valve stem guide of a needle-less injector in accordance with an embodiment of the instant invention.
Figure 13B:
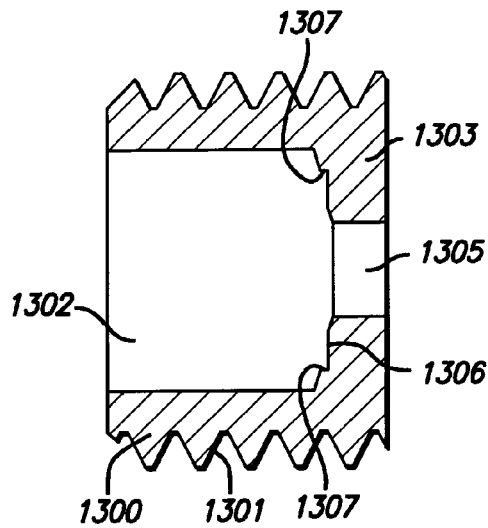
Figure 13C:
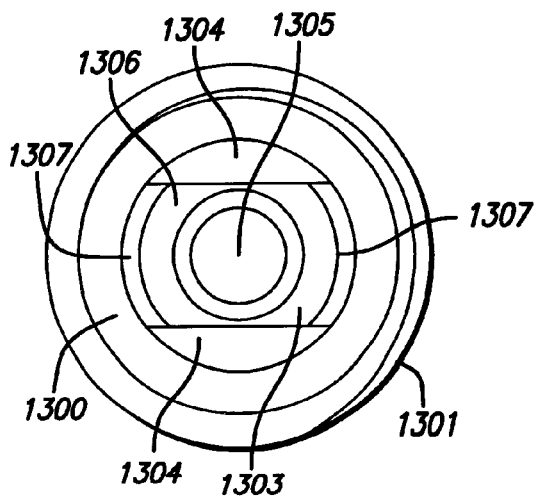
Figure 13D:
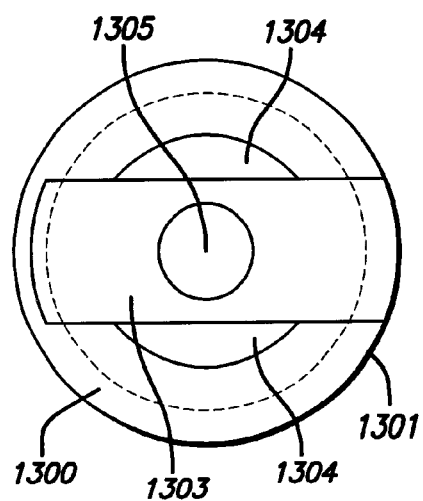

The closing ferrule 1200 is shown in FIG. 12 prior to its distal portion 1201 being mechanically bent around the closing rim 1101 and closing ridge 1006. The proximate portion 1202 of the closing ferrule 1200 is of substantially the same diameter as the exterior of the valve body 1100, such that solely bending the distal portion mechanically couples the valve body 1100 to the engine housing 1000. In FIG. 1, the distal portion 1201 of the closing ferrule 1200 is shown in the bent state. The valve body 1000 preferably has a depression 1102 around its circumference adapted to fit a gasket 1103 (shown in FIG. 1b). The gasket 1103 helps ensure that an airtight seal is maintained between the interior of the engine housing 1000 which contains the gas and the internal atmosphere of the needle-less injector 100.

Referring to FIG. 1, the interior of the valve body 1100 is preferably hollow and comprised of several distinct portions. The distal interior portion 1104 of the valve body 1100 may contain a screw thread engagement 1105, preferably extending from the distal end of the valve body 1100 to the distal end of a first axial cavity 1106. The first axial cavity 1106 may be bounded on its proximate end by a shoulder 1107 that separates this first axial cavity 1106 from a second axial cavity 1108, which is preferably of smaller diameter than the first axial cavity 1106. In preferred embodiments, the shoulder 1107 is an angled edge. Also in preferred embodiments, at least one valve stem guide 1109 protrudes from the wall of the second axial cavity 1108. In a most preferred embodiment, there are at least three such valve stem guides 1109 that serve to substantially prevent the valve stem 1400 from moving in any direction other than along the central axis of the needle-less injector 100 during administration of an injection.

The proximate end of the second axial cavity 1108 preferably terminates at a diffuser-receiving chamber 1110 that is of sufficient diameter such that it encircles a distal end 602 of the diffuser 600. After administration of an injection with the needle-less injector 100, the distal end 602 of the diffuser 600 is most preferably at rest within the diffuser-receiving chamber 1110.

The proximate end of the diffuser-receiving chamber 1110 preferably has at least one grip 1111 extending therefrom. Preferably, the at least one grip 1111 locks around another suitable element of a needle-less injector 100 as the gripping element 1112 is situated on the interior side of the grip 1111. In alternative embodiments, however, the at least one grip 1111 may lock within another element as the gripping element 1112 may be disposed on the exterior side of the grip 1111. In most preferred embodiments, there are two grips 1111 disposed opposite one another each of which contains a gripping element 1112 situated on the interior side of the grip 1111. In these most preferred embodiments, the two grips 1111 are slid over and lock around the locking ring 605 of the diffuser 600 upon administration of an injection. The combination of a locking ring 605 and grips 1111 assists in mitigating the kickback associated with deploying the compressed gas stored in the engine assembly 101 and ensures that a user fully and properly depresses the trigger 800, since an injection is preferably not deployed until the grips 1111 slip past the locking ring 605.

The valve body 1100 preferably further contains a threaded valve guide 1300, as depicted in FIG. 13. The threaded valve guide 1300 is preferably cylindrical in shape and threaded around its exterior wall 1301, such that it may be screwed into the distal interior portion 1104 of the valve body 1100 by interacting with the screw thread engagement 1105. Most preferably, the threading on the exterior wall 1301 of the threaded valve guide 1300 extends along the entirety of the exterior wall 1301 from the distal to the proximate end of the threaded valve guide 1300. The threaded valve guide 1300 may also contain a cylindrical interior cavity 1302 that is unobstructed at the proximate end. The distal end, however, is preferably partially covered with a valve stem guide pane 1303. The valve stem guide pane 1303 preferably provides at least one vent 1304 allowing gaseous communication between the interior cavity 1302 of the threaded valve guide 1300 and the hollow interior chamber 1003 of the engine housing 1000 at the distal end of the threaded valve guide 1300. Also preferably, the valve stem guide pane 1303 includes a hole 1305 at the central axis slightly larger in diameter than the valve stem 1400 that resides therein. Most preferably, the valve stem guide pane 1303 further includes a spring seat 1306 on its proximate surface that is comprised of at least one ridge 1307 that maintains the valve spring 1500 in proper position.

Figure 14A:
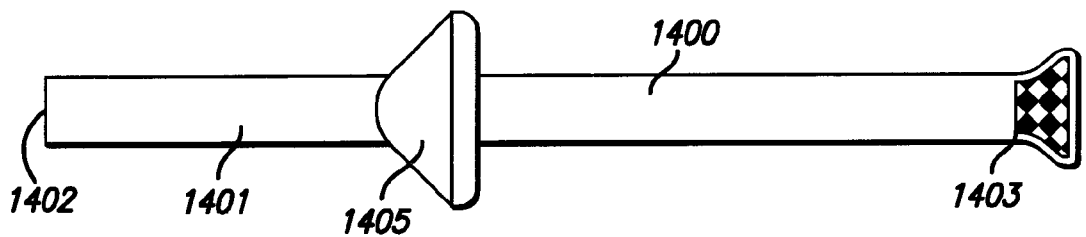
FIGS. 14a–c illustrate the valve stem of a needle-less injector in accordance with an embodiment of the instant invention.
Figure 14B:
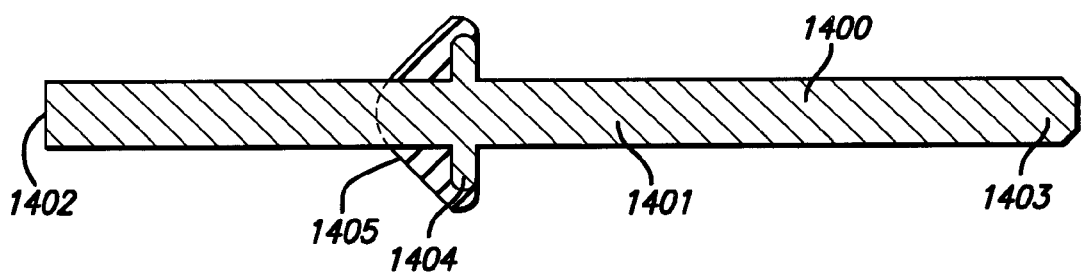
Figure 14C:
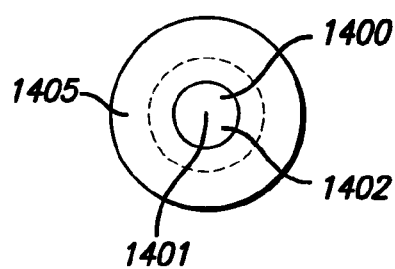

The valve body 1100 preferably further contains a valve stem 1400, as depicted in FIG. 14. The valve stem 1400 is preferably comprised of a substantially cylindrical rod 1401 having a proximate end 1402 which is flat and a distal end 1403 which is preferably pressed or hammer-forged. The distal end 1403 is shown after hammer-forging in FIG. 14*a* and prior to hammer-forging in FIG. 14*b*. Most preferably, there is also included a spring ridge 1404 that extends radially from the rod 1401, and a roughly conical valve head 1405 affixed to the proximate and exterior surfaces of the spring ridge 1404 as well as that portion of the rod 1401 immediately proximate to the spring ridge 1404. Most preferably, the valve head 1405 is comprised of a rubber material such as semi-permeable, silicon-based rubber that is sufficiently malleable for use in accordance with the needle-less injector 100. In most preferred embodiments, the angle between the proximate surface of the valve head 1405 and the central axis is substantially similar to the angle of the shoulder 1107 located between the first axial cavity 1106 and second axial cavity 1108 of the valve body 1100.

The valve body 1100 may further contain a valve spring 1500, as depicted in FIG. 15. The valve spring 1500 is preferably composed of wire and semi-conical in shape, wherein the proximate end 1501 is smaller in diameter than the distal end 1502. The proximate end 1501 of the valve spring 1500 preferably rests against the distal surface of the spring ridge 1404 on the valve stem 1400, while the distal end 1502 of the valve spring 1500 preferably rests against the proximate surface of the valve stem guide pane 1303 and is held in place radially by the spring seat 1306.

Furthermore, the valve of the instant invention may be repeatedly opened and closed without being destroyed, thus it may be inspected for quality control determinations by opening and closing at least one time prior to the engine assembly 101 being filled with compressed gas. A faulty valve is a concern in any device employing such a mechanism, though it is of particular import in the context of a needle-less injector useful in medical applications, where such a faulty valve may result in the improper dosage of medication.

During the administration of an injection with the needle-less injector, several mechanisms act to mitigate the kickback associated with releasing compressed gas from the engine housing. The grips on the valve body operatively couple with the locking ring on the exterior surface of the diffuser and the retainer hooks on the retainer hook mechanisms operatively lock at each successive saw tooth of the latch retainer mechanisms. Such safety features not only function to avoid potential injury, but further insure proper delivery of liquid through an injection surface.

EXAMPLE

Operation of a Needle-less Injector

Prior to use, a needle-less injector is assembled in accordance with the instant invention, all elements thereof being gamma sterilized with the exception of the engine assembly. The engine assembly is checked for quality control purposes by opening and closing the valve, and thereafter the engine housing is filled with a suitable compressed gas. The interior portion of the housing between the proximate end of the housing and the proximate end of the plunger is then filled with 0.5 ml. of liquid. The needle-less injector is then assembled and stored for a prolonged period of time.

When ready for use (see FIG. 1*a*), the ampoule cap is removed from the proximate end of the housing by the user. Subsequently, the user also removes the safety clamp by bending and/or distorting the clamp. The user is performing self-administration of an injection and elects to employ the following configuration: the user's index and middle fingers are placed in the arcs of the finger rests for stabilization of the device, with the thumb operably placed against the trigger. The proximate end of the needle-less injector is then positioned roughly perpendicular to the injection surface.

The user then depresses the trigger until the proximate end of the trigger comes to rest against the ridge defining the proximate end of the clamp indentation. During this movement of the trigger, the retainer hook mechanisms and latch retainer mechanisms interact as the retainer hooks lock past consecutive saw teeth that comprise the latch retainer mechanisms.

Forward, axial movement of the trigger causes the engine housing, valve body and threaded valve guide to move, as well. Thus, the grips at the proximate end of the valve body proceed to lock around the locking ring of the diffuser as the distal portion of the diffuser concurrently slides into and partially through the diffuser-receiving cavity of the valve body, coming to rest therein. Simultaneously, the valve stem moves along with the trigger, however, once it comes into mechanical contact with the valve stem support depression in the diffuser it remains stationary relative to the housing. The valve stem and diffuser reach such mechanical contact approximately when the grips slide over and past the locking ring of the diffuser.

When the valve stem and diffuser come into mechanical contact, the valve spring is compressed and the valve opens as the valve head is separated from the shoulder residing between the first and second axial cavities of the valve body. Compressed gas (previously stored in the engine housing, the interior cavity of the threaded valve guide and the first axial cavity of the valve body) may then rush through the gap created between the valve head and the shoulder. The gas rushes through the second axial cavity, past the valve stem guides, through the diffuser-receiving chamber and through the at least one channel in the diffuser. The gas then fills the space defined by the diffuser cup and the expansion cup of the piston, which rest near or against one another prior to gas forcing the two elements apart. The introduction of gas into this space forces the piston in the proximate direction, pushing the plunger through the interior of the housing and correspondingly forcing the liquid from the injector through the at least one orifice in the proximate end of the injector and into and/or through the injection surface. The piston and plunger act in concert as a driver. Once the plunger comes to rest against the proximate end of the housing, excess gas may escape through the exhaust passage in the housing. The user may then dispose of the needle-less injector, the injection having been completed.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A needle-less injector suitable for injecting a fluid through a surface, said needle-less injector comprising:
    a housing containing the fluid, said housing further containing at least one orifice;
    a diffuser affixed to said housing, said diffuser having disposed therein at least one channel;
    an engine fitted within said housing, said engine further containing a gas;
    a driver that forces said fluid out of said housing, said driver being slidably disposed within said housing;
    a trigger coupled to said housing; and
    a valve attached to said engine;
    wherein depression of said trigger causes said valve to open; and
    wherein said valve can survive being repeatedly opened.

2. The needle-less injector in accordance with claim 1, said valve comprising:
    a valve stem having a circular ridge;
    a valve head affixed to said valve stem and said circular ridge;
    a valve stem guide pane affixed to said engine; and
    a spring having a first end resting against said circular ridge and a second end resting against said valve stem guide pane.

3. The needle-less injector in accordance with claim 1, said driver comprising:
    a piston; and
    a plunger.

4. The needle-less injector in accordance with claim 3, wherein
    said plunger is symmetrical; and
    said plunger forms a substantially airtight seal with said housing.

5. The needle-less injector in accordance with claim 3, said plunger comprising:
    a conical front end;
    a conical back end; and
    a cylindrical body.

6. The needle-less injector in accordance with claim 5, said plunger further comprising at least one ridge surrounding said cylindrical body.

7. The needle-less injector in accordance with claim 3, said piston comprising an expansion cup.

8. The needle-less injector in accordance with claim 1, further comprising an ampoule cap removably attached to said housing, wherein said ampoule cap forms an airtight seal over said orifice of said housing.

9. The needle-less injector in accordance with claim 1, said housing further comprising an exhaust passage.

10. The needle-less injector in accordance with claim 1, said trigger further comprising an end with a non-slip surface.

11. The needle-less injector in accordance with claim 1, said trigger further comprising at least one retainer hook mechanism and said housing further comprising at least one latch retainer mechanism.

12. The needle-less injector in accordance with claim 1, said diffuser further comprising a locking ring and said engine further comprising at least one grip to lock around said locking ring.

13. The needle-less injector in accordance with claim 1, further comprising a safety clamp removably attached to said housing, wherein said safety clamp prevents said trigger from moving relative to said housing in the axial direction of said at least one orifice.

14. The needle-less injector in accordance with claim 1, said housing further comprising at least one finger rest.

15. The needle-less injector in accordance with claim 1, said housing further comprising two finger rests disposed opposite one another, said finger rests further comprising a non-slip surface.

16. A needle-less injector suitable for injecting a fluid through a surface, said needle-less injector comprising:

a housing containing the fluid, said housing further containing at least one orifice;

a diffuser affixed to said housing, said diffuser having disposed therein at least one channel;

an engine fitted within said housing, said engine further containing a gas;

a driver that forces said fluid out of said housing, said driver being slidably disposed within said housing;

a trigger coupled to said housing; and at least one grip disposed on said engine, said grip adapted to lock with an element of a needle-less injector.

17. The needle-less injector in accordance with claim 16, said engine further comprising a valve.

18. The needle-less injector in accordance with claim 17, and said valve comprising:

a valve stem having a circular ridge;

a valve head affixed to said valve stem and said circular ridge;

a valve stem guide pane affixed to said engine; and a spring having a first end resting against said circular ridge and a second end resting against said valve stem guide pane.

19. The needle-less injector in accordance with claim 18, wherein said valve opens upon depression of said trigger.

20. The needle-less injector in accordance with claim 16, said driver comprising:

a piston; and a plunger.

21. The needle-less injector in accordance with claim 20, wherein said plunger is symmetrical; and said plunger forms a substantially airtight seal with said housing.

22. The needle-less injector in accordance with claim 20, said plunger comprising:

a conical front end;

a conical back end; and a cylindrical body.

23. The needle-less injector in accordance with claim 22, said plunger further comprising at least one ridge surrounding said cylindrical body.

24. The needle-less injector in accordance with claim 20, said piston comprising an expansion cup.

25. The needle-less injector in accordance with claim 16, further comprising an ampoule cap removably attached to said housing, wherein said ampoule cap forms an airtight seal over said orifice of said housing.

26. The needle-less injector in accordance with claim 16, said housing further comprising an exhaust passage.

27. The needle-less injector in accordance with claim 16, said trigger further comprising an end with a non-slip surface.

28. The needle-less injector in accordance with claim 16, said trigger further comprising at least one retainer hook mechanism and said housing further comprising at least one latch retainer mechanism.

29. The needle-less injector in accordance with claim 16, said diffuser further comprising a locking ring and said needle-less injector comprising at least two grips to lock around said locking ring, said locking ring being said element of said needle-less injector with which said grips are adapted to lock.

30. The needle-less injector in accordance with claim 16, further comprising a safety clamp removably attached to said housing, wherein said safety clamp prevents said trigger from moving relative to said housing in the axial direction of said at least one orifice.

31. The needle-less injector in accordance with claim 16, said housing further comprising at least one finger rest.

32. The needle-less injector in accordance with claim 16, said housing further comprising two finger rests disposed opposite one another, said finger rests further comprising a non-slip surface.

33. A needle-less injector suitable for injecting a fluid through a surface, said needle-less injector comprising:

a housing containing the fluid, said housing further containing at least one orifice;

an engine fitted within said housing, said engine containing a gas and including a valve, said valve including:

a valve stem having a circular ridge; and a valve head affixed to said valve stem and said circular ridge;

a driver that forces said fluid out of said housing, said driver being slidably disposed within said housing; and a diffuser affixed to said housing, said diffuser having a locking ring and said engine further including at least one grip to lock around said locking ring.

34. The needle-less injector in accordance with claim 33, further including:

at least one latch retainer mechanism disposed on the exterior of said housing;

a trigger coupled to said housing; and at least one retainer hook mechanism disposed on said trigger, said at least one retainer hook mechanism being aligned to interact with said latch retainer mechanism, wherein said valve opens upon depression of said trigger.

35. The needle-less injector in accordance with claim 33, said engine further including:

a valve stem guide pane affixed to said engine; and a spring having a first end resting against said circular ridge and a second end resting against said valve stem guide pane.

36. The needle-less injector in accordance with claim 33, further including a safety clamp removably attached to said housing, wherein said safety clamp prevents said trigger from moving relative to said housing in the axial direction of said at least one orifice.

37. The needle-less injector in accordance with claim 33, said housing further including at least one finger rest.

38. A needle-less injector suitable for injecting a fluid through a surface, said needle-less injector comprising:

a housing containing the fluid, said housing having at least one orifice;

a diffuser affixed to said housing, said diffuser having disposed therein at least one channel;

an engine fitted within said housing, said engine containing a gas; and a driver that forces said fluid out of said housing, said driver being slidably disposed within said housing and including:

a piston; and a plunger, said plunger having:

a conical front end;

a conical back end; and a cylindrical body.

39. The needle-less injector in accordance with claim 38, wherein said plunger is symmetrical along a plane perpendicular to a central axis; and said plunger forms a seal with said housing.

40. The needle-less injector in accordance with claim 38, said plunger including at least one ridge surrounding said cylindrical body.

41. The needle-less injector in accordance with claim 38, wherein said piston includes an expansion cup.

42. The needle-less injector in accordance with claim 38, further including:
- at least one latch retainer mechanism disposed on the exterior of said housing;
- a trigger coupled to said housing; and
- at least one retainer hook mechanism disposed on said trigger, said at least one retainer hook mechanism being aligned to interact with said latch retainer mechanism.

43. The needle-less injector in accordance with claim 38, wherein said housing includes at least one finger rest.

44. A needle-less injector suitable for injecting a fluid through a surface, said needle-less injector comprising:
- a housing containing the fluid, said housing containing at least one orifice;
- an engine fitted within said housing, said engine containing a gas; and
- a driver that forces said fluid out of said housing, said driver being slidably disposed within said housing and including:
  - a piston; and
  - a plunger, said plunger having an expansion cup.

45. The needle-less injector in accordance with claim 44, wherein
- said plunger is symmetrical along a plane perpendicular to a central axis; and
- said plunger forms a seal with said housing.

46. The needle-less injector in accordance with claim 44, wherein said plunger includes at least one ridge surrounding said cylindrical body.

47. The needle-less injector in accordance with claim 44, further including:
- at least one latch retainer mechanism disposed on the exterior of said housing;
- a trigger coupled to said housing; and
- at least one retainer hook mechanism disposed on said trigger, said at least one retainer hook mechanism being aligned to interact with said latch retainer mechanism, wherein said valve opens upon depression of said trigger.

48. The needle-less injector in accordance with claim 44, wherein said housing includes at least one finger rest.

* * * * *